(12) United States Patent
Holley et al.

(10) Patent No.: US 12,728,219 B2
(45) Date of Patent: Sep. 8, 2026

(54) ACOUSTIC ANALYSIS OF A RESPIRATORY THERAPY SYSTEM

(71) Applicants: ResMed Pty Ltd, Bella Vista (AU); ResMed Sensor Technologies Limited, Clonskeagh (IE)

(72) Inventors: Liam Holley, Sydney (AU); Redmond Shouldice, Clonskeagh (IE); Anna Rice, Clonskeagh (IE); Niall Fox, Clonskeagh (IE); Stephen Mcmahon, Clonskeagh (IE); Graeme Lyon, Clonskeagh (IE)

(73) Assignees: ResMed Pty Ltd (AU); ResMed Sensor Technologies Limited (IE)

( * ) Notice: Subject to any disclaimer, the term of this patent is extended or adjusted under 35 U.S.C. 154(b) by 970 days.

(21) Appl. No.: 17/760,663

(22) PCT Filed: Sep. 30, 2020

(86) PCT No.: PCT/AU2020/051037
§ 371 (c)(1),
(2) Date: Mar. 15, 2022

(87) PCT Pub. No.: WO2021/062466
PCT Pub. Date: Apr. 8, 2021

(65) Prior Publication Data

US 2022/0339383 A1 Oct. 27, 2022

Related U.S. Application Data

(60) Provisional application No. 62/908,364, filed on Sep. 30, 2019.

(30) Foreign Application Priority Data

Oct. 9, 2019 (AU) ................................ 2019903799

(51) Int. Cl.
*A61M 16/00* (2006.01)
*A61M 16/08* (2006.01)
(Continued)

(52) U.S. Cl.
CPC ...... *A61M 16/026* (2017.08); *A61M 16/0003* (2014.02); *A61M 16/0069* (2014.02);
(Continued)

(58) Field of Classification Search
CPC ..... A61B 5/7257; A61B 5/087; A61B 5/7275; A61B 5/082; A61M 2205/42;
(Continued)

(56) References Cited

U.S. PATENT DOCUMENTS 863,814 A 8/1907 Underwood
4,944,310 A 7/1990 Sullivan
(Continued)

FOREIGN PATENT DOCUMENTS

CN 102316919 A 1/2012
CN 109152551 A 1/2019
(Continued)

OTHER PUBLICATIONS

Berton C, Cholley B. Equipment review: new techniques for cardiac output measurement—oesophageal Doppler, Fick principle using carbon dioxide, and pulse contour analysis. Crit Care. Jun. 2002;6(3):216-21. doi: 10.1186/cc1492. Epub Apr. 25, 2002. PMID: 12133181; PMCID: PMC137448. (Year: 2002).*
(Continued)

*Primary Examiner* — Brandy S Lee
*Assistant Examiner* — Rohan Patel
(74) *Attorney, Agent, or Firm* — Botos Churchill IP Law LLP

(57) ABSTRACT

Method and apparatus obtain information about a patient and/or a respiratory therapy system that is configured to
(Continued)

deliver respiratory therapy to the patient. The respiratory therapy system may include a flow generator configured to generate a supply of pressurized air along an air circuit to a patient interface. A sound signal representing a sound in the air circuit may be processed to obtain cepstrum data. A time series of delay estimates based on acoustic signatures of the cepstrum data may be generated. Each acoustic signature may represent a reflection of sound from a patient interface along the air circuit. Variation in the time series of delay estimates may be analysed. One or more output indicators based on the variation may be generated. The one or more output indicators may concern patient and/or system status.

63 Claims, 19 Drawing Sheets

(51) Int. Cl.

| | |
|---|---|
| ***G10L 21/0224*** | (2013.01) |
| ***G10L 21/0308*** | (2013.01) |
| ***G10L 25/24*** | (2013.01) |
| ***G10L 25/63*** | (2013.01) |
| ***G16H 20/40*** | (2018.01) |
| ***G16H 40/63*** | (2018.01) |
| *A61M 16/06* | (2006.01) |

(52) U.S. Cl.
CPC ..... *A61M 16/0875* (2013.01); *G10L 21/0224* (2013.01); *G10L 21/0308* (2013.01); *G10L 25/24* (2013.01); *G10L 25/63* (2013.01); *G16H 20/40* (2018.01); *G16H 40/63* (2018.01); *A61M 16/06* (2013.01); *A61M 2205/3375* (2013.01); *A61M 2205/502* (2013.01); *A61M 2230/04* (2013.01); *A61M 2230/42* (2013.01); *A61M 2230/432* (2013.01)

(58) Field of Classification Search
CPC .............. A61M 16/024; A61M 16/026; A61M 2205/3375; G10L 25/24; G10L 21/0224; G16H 40/63
See application file for complete search history.

(56) References Cited

U.S. PATENT DOCUMENTS

| | | | | |
|---|---|---|---|---|
| 6,290,654 | B1 * | 9/2001 | Karakasoglu .......... | A61B 7/003 600/529 |
| 7,866,944 | B2 | 1/2011 | Barton et al. | |
| 8,636,479 | B2 | 1/2014 | Barton et al. | |
| 2001/0029339 | A1 | 10/2001 | Orr et al. | |
| 2006/0037615 | A1 * | 2/2006 | Wilkinson ............. | A61B 5/085 128/204.23 |
| 2008/0251070 | A1 * | 10/2008 | Pinskiy ................. | A61M 16/04 128/202.22 |
| 2011/0313689 | A1 * | 12/2011 | Holley ................ | A61M 16/024 702/56 |
| 2016/0184546 | A1 * | 6/2016 | Heinonen .......... | A61M 16/024 128/204.22 |
| 2019/0105011 | A1 | 4/2019 | Kim et al. | |

FOREIGN PATENT DOCUMENTS

| | | | |
|---|---|---|---|
| JP | 2001506158 | A | 5/2001 |
| JP | 2012517303 | A | 8/2012 |
| JP | 2017507676 | A | 3/2017 |
| WO | 2010091462 | A1 | 8/2010 |
| WO | 2013020167 | A1 | 2/2013 |
| WO | 2013149138 | A1 | 10/2013 |
| WO | 2015110374 | A1 | 7/2015 |
| WO | 2018050913 | A1 | 3/2018 |
| WO | 2020092701 | A2 | 5/2020 |

OTHER PUBLICATIONS

Extended European Search Report from corresponding EP Application No. 20870657.2 dated Oct. 9, 2023 (6 pp.).
PCT Notification of Transmittal of the International Search Report and the Written Opinion of the International Searching Authority, or the Declarations issued in PCT application No. PCT/AU2020/051037 on Dec. 15, 2020.
Childers, Donald G, et al., "The Cepstrum: A Guide to Processing"; Proceedings of the IEEE, vol. 65, No. 10, Oct. 1977.
Randall, RB, "Frequency Analysis", Copenhagen: Bruel & Kjaer, p. 344 (1977, revised ed. 1987).
West, John B, "Respiratory Physiology", Lippincott Williams & Wilkins, 9th edition published 2011.
Office Action issued in corresponding Japanese Patent Application No. 2022-520082, mailed Jul. 26, 2024, 8 pages.
Office Action issued in corresponding Japanese Patent Application No. 2022-520082, mailed Jul. 4, 2025, 6 pages.
Office Action issued in corresponding Chinese Patent Application No. 202080080122.X, mailed Jun. 13, 2025, 40 pages.
Examination Report No. 1 in AU Application No. 2020359289, dated Apr. 16, 2025. 3 Pages.
Examination Report No.2 issued in corresponding Australian Patent Application No. 2020359289, mailed Jan. 7, 2026, 2 pages.
Office Action issued in corresponding Chinese Patent Application No. 202080080122.X, mailed Mar. 6, 2026, 72 pages.

* cited by examiner

Copyright 2012 ResMed Limited

ACOUSTIC ANALYSIS OF A RESPIRATORY THERAPY SYSTEM

1 CROSS-REFERENCE TO RELATED APPLICATIONS

The present application is a national phase entry under 35 U.S.C. § 371 of International Application No. PCT/AU2020/051037, filed Sep. 30, 2020, published in English, which claims the benefit of U.S. Provisional Application No. 62/908,364, filed 30 Sep. 2019, and of Australian Provisional Application No. 2019903799, filed Oct. 9, 2019, the entire disclosure of each of which is hereby incorporated herein by reference.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Obstructive Sleep Apnea (OSA) is a respiratory disorder characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods known as apneas, typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various therapies, such as Continuous Positive Airway Pressure (CPAP) therapy, high flow therapy (HFT), non-invasive ventilation (NIV) and invasive ventilation (IV) have been used to treat one or more of the above respiratory disorders.

2.2.3 Therapy Systems

These therapies may be provided by a respiratory therapy system or device. Such systems and devices may also be used to diagnose a condition without treating it.

A respiratory therapy system may comprise a Respiratory Therapy Device (RT device), an air circuit, a humidifier, a patient interface, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

2.2.3.2 Respiratory Therapy (RT) Device

A respiratory therapy (RT) device, such as a respiratory pressure therapy (RPT) device, may be used to deliver one or more of a number of therapies described above, such as by generating a flow of air for delivery to an entrance to the airways. The flow of air may be pressurised. Examples of RPT devices include a CPAP device and a ventilator. A respiratory therapy (RT) device in some cases may be a high flow therapy (HFT) device, which provides a high flow respiratory therapy.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices.

Examples of RPT devices include the S9 Sleep Therapy System, manufactured by ResMed Limited, ventilators such as the ResMed Stellar™ Series of Adult and Paediatric Ventilators and the ResMed Astral™ 150 ventilator.

2.2.3.3 Air Circuit

An air circuit is a conduit or a tube constructed and arranged to allow, in use, a flow of air to travel between two components of a respiratory therapy system such as the RT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RT device and the patient interface produces humidified gas that minimizes drying of the nasal mucosa and increases patient airway comfort. In addition, in cooler climates, warm air applied generally to the face area in and about the patient interface is more comfortable than cold air.

2.2.3.5 Vent Technologies

Some forms of respiratory therapy systems may include a vent to allow the washout of exhaled carbon dioxide. The vent may allow a flow of gas from an interior space of a patient interface, e.g., the plenum chamber, to an exterior of the patient interface, e.g., to ambient.

2.2.3.6 Sensing and Data Management

A patient, a caregiver, a clinician, an insurance company or a technician may wish to collect data in relation to a respiratory therapy, whether they relate to the patient, individual components used for therapy, or the therapy system as a whole. There exist numerous situations in providing respiratory therapy to a patient where one or more parties involved therein may benefit from collection of therapy related data, and leveraging the collected data.

2.2.4 Component Identification

As previously mentioned, a respiratory therapy system typically includes an RPT device, a humidifier, an air circuit, and a patient interface. A variety of different forms of patient interface may be used with a given RPT device, for example a nasal pillows, nasal prongs, nasal mask, nose & mouth (oronasal) mask, or full face mask. Furthermore, different types of conduit (length, diameter) may be used, such as in an air circuit. In order to provide improved control of therapy delivered to the patient interface, it may be advantageous to estimate treatment parameters such as pressure in the patient interface, leak flow rate, and vent flow rate. In systems using estimation of treatment parameters, knowledge of the type of component being used by a patient can enhance the accuracy of treatment parameter estimation, and therefore the efficacy of therapy. To obtain that knowledge, some RPT devices include a menu system that allows the patient to select the type of system components, including the patient interface, being used, e.g., brand, form, model, etc. Once the types of the components are entered by the patient, the RPT device can select appropriate operating parameters of the flow generator that best coordinate with the selected components, and can more accurately monitor treatment parameters during therapy. However, patients may not enter the types of components correctly, or at all, leaving the RPT device in error or ignorant about the type of component in use.

Some components of a respiratory therapy system need to be replaced at a higher frequency than others for effective therapy. For example, a patient interface comprising a silicone seal-forming portion may be replaced by some patients in periods of months (e.g. 3 months), whereas RT devices may be replaced or upgraded every few years (e.g. 3 years). For those components that are to be replaced at relatively frequent intervals (e.g. a patient interface), a patient or caregiver regularly faces challenges in being reliably and accurately notified, at a low cost, when their component is due to be replaced. When it is replaced, one or more settings in the therapy system (e.g. a software setting in the RT device) may need to be changed to ensure that the system is taking full advantage of the new component. The ability to automatically identify components of a respiratory therapy system is therefore important both for optimising therapy and for keeping patients and caregivers informed about replacement timing.

In the past, an array of solutions have been employed, or proposed, in the field of respiratory therapy in relation to component identification. For example, sensors/transducers have been used, and proposed, in a plethora of forms to collect data in relation to environmental conditions, information in relation to the patient, identification of components, therapy operating conditions or the like. Indeed, many RT devices comprise one or more sensors, such as a flow rate sensor, a pressure sensor, a humidity sensor, a temperature sensor and the like. Signals generated by such sensors may be analysed to generated therapy related data such as the identity of particular components, such as patient interfaces, in the respiratory therapy system.

However, sensors/transducers typically require a suite of additional componentry, which may hinder their adoption in many forms. For instance, data collected by the sensors/transducers must then be communicated to be saved and/or analysed, for example from the sensor to a memory and/or a processor. This, and the aforementioned sensors, may further increase cost of design, testing, and/or manufacturing to the medical device manufacturer, and/or may increase the cost and complexity to the patient.

In addition, integrating costly electrical and/or mechanical features to the frequently replaced component(s), such as the patient interface, may be detrimental to providing a most cost-effective therapy, and potentially environmentally unsustainable due to the increased waste.

Furthermore, many proposed solutions in relation to sensors and/or transducers may be limited in that if a sensor is proposed to be located remotely from where its data is to be saved and/or analysed, often this may further increase a complexity and/or cost of implementation. For example, where a patient interface comprises a sensor, it may require an electrical connection to the RT device, which may further increase complexity and/or cost of implementation.

Also, designers of RT devices face numerous choices, and often arrive at different solutions when compared to other devices on the market such as by a competitor, or indeed, by the same manufacturer but produced at a different time. As a result, the associated electrical connector provided may be only connectible to a particular RT device. This may have an unintended effect of creating incompatibility which can be a disadvantage to a particular sub-segment of consumers, and/or it may reduce consumer choice.

2.2.5 Exhaled Gas Composition

The composition of a patient's exhaled gas is a useful indicator of the state of a patient's health. In particular, capnography sensors are configured to measure the fractional concentration of exhaled carbon dioxide for diagnostic and monitoring purposes, for example during anaesthesia and intensive care, or over longer periods for the progression of COPD.

Cardiac output is an important hemodynamic parameter of a patient. It can be used by a physician, clinician, technician, care giver, and the like to define a therapy and/or evaluate a patient's response to medical therapy or intervention. Cardiac output describes the volume of blood being pumped by the heart per unit time. It is the product of heart rate (HR) and the stroke volume (SV). HR is the number of beats per unit time, such as the number of beats per minute (bpm). SV is the volume of blood pumped from the ventricle per beat. Typically, cardiac output is provided in units of liters per minute (L/min).

The Fick method is an approach used for determining cardiac output. It involves the measurement of oxygen ($O_2$), carbon dioxide ($CO_2$), and para-aminohippuric acid (PAH). Usually, the Fick method involves monitoring oxygen consumption in a closed space to calculate the carbon dioxide exchange. However, cardiac output can be estimated using a modified Fick method. The modified Fick method is related to carbon dioxide generation, with an assumption that oxygen consumption and carbon dioxide generation have a known relationship (such as a linear relationship).

Capnography sensors are expensive to incorporate in a respiratory therapy system and even when present, may have such a large latency as to be unsuitable for real-time $CO_2$ monitoring. It may therefore be desirable for a respiratory system to have a low-cost way of estimating the concentration of $CO_2$ in its air circuit, and even more desirably, one capable of supporting such an estimation in close to real time.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use, patient engagement, and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

The present technology may provide improvements to known apparatus to obtain useful information about a respiratory therapy system through acoustic analysis, in particular by analysis of time variations of a delay of an acoustic reflection signature on different time scales. According to one example, variations of the delay in the breathing frequency band may provide a measure of exhaled carbon dioxide concentration, which in turn may be used for diagnostic and therapeutic purposes such as estimating a patient's cardiac output.

Some implementations of the present technology include a method of one or more processors for generating a patient and/or system status indication with a respiratory therapy system configured to deliver respiratory therapy to a patient. The respiratory therapy system may include a flow generator configured to generate a supply of pressurized air along an air circuit to a patient interface. The method may include processing a sound signal representing a sound in the air circuit from a microphone to obtain cepstrum data. The method may include generating a time series of delay estimates based on acoustic signatures of the cepstrum data. Each of the acoustic signatures may represent a reflection of sound from the patient interface along the air circuit. The method may include analysing variation of the time series of delay estimates. The method may include generating one or more output indicators based on the variation, the one or more output indicators concerning patient and/or system status.

In some implementations, generating the time series may include separating an acoustic signature from a cepstrum of the cepstrum data. Generating the time series may include estimating a delay of the acoustic signature for the time series of delay estimates. Generating the time series may include repeating the separating, and estimating. The analysing may include filtering the time series of delay estimates to allow passing of frequencies within a breathing rate frequency band. The analysing may further include converting the time series of delay estimates to indications of concentration of carbon dioxide in the air circuit. The one or more output indicators may include an indication of end-tidal carbon dioxide concentration ($EtCO_2$) of the patient. The method may further include adjusting a parameter of the respiratory therapy system based on the indication of $EtCO_2$.

In some implementations, the one or more output indicators may include an estimate of cardiac output of the patient. The method may further include applying a modified Fick technique function and measuring change in an indication of $EtCO_2$ generated with the time series of delay estimates to generate the estimate of the cardiac output. The method may further include repeating the analysing to generate a plurality of estimates of the patient's cardiac output. The method may further include determining a trend in the plurality of estimates of the patient's cardiac output. The method may further include taking action based on the determined trend in the plurality of estimates. The taking action may include generating an output communication and/or an output on a display. The analysing may further include: determining one or more environmental parameters of the respiratory therapy system; and correcting for the one or more environmental parameters during the determining the carbon dioxide concentration. The one or more environmental parameters may include air temperature, ambient pressure, ambient carbon dioxide concentration, background noise, or a combination thereof. The background noise may be generated by a sound sensor that may be different from a sound sensor that generated the sound signal.

In some implementations, the analysing may include removing breathing-rate-frequency-band variations from the time series of delay estimates to obtain a time series of non-respiratory-related delay estimates. The one or more output indicators may include an indication of replacement condition of a component of the air circuit and/or the patient interface. The analysing may further include mapping the time series of non-respiratory-related delay estimates to a time series of values of length of the air circuit. The analysing may further include determining whether an increase in length of the air circuit over many therapy sessions may be greater than a threshold. The analysing may further include determining a variability of length of the air circuit over a session of respiratory therapy. The processing may include removing background noise from the environment of the respiratory therapy system from the sound signal.

In some implementations, the one or more output indicators further may include (a) a control signal for controlling an adjustment of a therapy output of a therapy device; and/or (b) an output communication or an output of a display.

Some implementations of the present technology include a device for generating a patient and/or a system status indication with a respiratory therapy system configured to deliver respiratory therapy to a patient, the respiratory therapy system may include a flow generator configured to generate a supply of pressurized air along an air circuit to a patient interface. The device may include a sensor configured to generate a sound signal representing a sound in the air circuit. The device may include a controller may include one or more processors and a memory. The one or more processors may be configured by program instructions stored in the memory to execute any one or more of the method aspects described herein. In some implementations, the device may further include a blower, wherein the controller may be configured to control operation of the blower.

Some implementations of the present technology include a device for generating a patient and/or system status indication with a respiratory therapy system configured to deliver respiratory therapy to a patient, the respiratory therapy system may include a flow generator configured to generate a supply of pressurized air along an air circuit to a patient interface. The device may include a sensor configured to generate a sound signal representing a sound in the air circuit. The device may include a controller. The controller may be configured to process the sound signal representing a sound in the air circuit to obtain cepstrum data. The controller may be configured to generate a time series of delay estimates based on acoustic signatures in the cepstrum data. Each of the acoustic signatures may represent a reflection of sound from the patient interface along the air circuit. The controller may be configured to analyse variation in the time series of delay estimates. The controller may be configured to generate one or more output indicators based on the variation, the one or more output indicators concerning patient and/or system status.

In some implementations, the device may further include a second sensor configured to generate a sound signal representing background noise in an environment of the respiratory therapy system. The controller may be further configured to remove background noise from the environment of the respiratory therapy system from the generated sound signal representing the sound in the air circuit using the generated sound signal representing the background noise in the environment of the respiratory therapy system. To generate the time series, the controller may be configured to separate an acoustic signature from a cepstrum of the cepstrum data. To generate the time series, the controller may be configured to estimate a delay of the acoustic signature for the time series of delay estimates. To generate the time series, the controller may be configured to repeating the separation, and the estimation.

In some implementations, to analyse variation, the controller may be configured to filter the time series of delay estimates to allow passing of frequencies within a breathing rate frequency band. To analyse variation, the controller may be configured to convert the time series of delay estimates to indications of concentration of carbon dioxide in the air circuit. The one or more output indicators may include an indication of end-tidal carbon dioxide concentration ($EtCO_2$) of the patient. The controller may be further configured to adjust a parameter of the respiratory therapy system based on the indication of $EtCO_2$. The one or more output indicators may include an estimate of cardiac output of the patient. The controller may be configured to apply a modified Fick technique function and measure change in an indication of $EtCO_2$ generated with the time series of delay estimates to generate the estimate of the cardiac output. The controller may be configured to repeat the analysing to generate a plurality of estimates of the patient's cardiac output. The controller may be further configured to determine a trend in the plurality of estimates of the patient's cardiac output. The controller may be further configured to take action based on the determined trend in the plurality of estimates. The action may include generating an output communication and/or an output on a display. To analyse variation, the controller may be configured to remove breathing-rate-frequency-band variations from the time series of delay estimates to obtain a time series of non-respiratory-related delay estimates. The one or more output indicators may include an indication of replacement condition of a component of the air circuit and/or the patient interface.

In some implementations, to analyse variation, the controller may be configured to map the time series of non-respiratory-related delay estimates to a time series of values of length of the air circuit. To analyse variation, the controller may be configured to determine whether an increase in length of the air circuit over many therapy sessions may be greater than a threshold. To analyse variation, the controller may be configured to determine a variability of length of the air circuit over a session of respiratory therapy. The one or more output indicators further may include (a) a control signal for controlling an adjustment of a therapy output of a therapy device; and/or (b) an output communication or an output of a display.

Some implementations of the present technology include apparatus that may include means for generating a sound signal representing a sound in an air circuit of a respiratory therapy system, the respiratory therapy system may include a flow generator configured to generate a supply of pressurized air from an outlet along the air circuit to a patient interface. The apparatus may include means for processing the sound signal representing a sound in the air circuit, to obtain cepstrum data. The apparatus may include means for generating a time series of delay estimates based on based on acoustic signatures in the cepstrum data, wherein each of the acoustic signatures represents a reflection of sound from the patient interface along the air circuit. The apparatus may include means for analysing variation of the time series of delay estimates. The apparatus may include means for generating one or more output indicators based on the variation, the one or more output indicators concerning patient and/or system status.

Some implementations of the present technology include a method of one or more processors for generating a status indication about a patient interface associated with a respiratory therapy system configured to deliver respiratory therapy to a patient, the respiratory therapy system may include a flow generator configured to generate a supply of pressurized air along an air circuit to the patient interface. The method may include processing a sound signal representing a sound in the air circuit, to obtain cepstrum data. The method may include separating an acoustic signature from the cepstrum data, the acoustic signature representing a reflection of sound from the patient interface along the air circuit. The method may include estimating an internal delay of the acoustic signature, wherein the internal delay may be a delay between two portions of the acoustic signature representing reflections from respective components of the patient interface separated by a mask tube. The method may include repeating the processing, separating, and estimating to generate a time series of estimates of the internal delay. The method may include analysing the time series of internal delay estimates. The method may include generating one or more output indicators based on the analysing, the one or more output indicators concerning patient interface status.

In some implementations, the analysing may include filtering the time series of internal delay estimates to allow passing of frequencies within a breathing rate frequency band. The analysing may further include analysing the filtered time series of internal delay estimates to generate an indication of concentration of carbon dioxide in the mask tube. The analysing may include removing breathing-rate-frequency-band variations from the time series of internal delay estimates to obtain a time series of non-respiratory-related internal delay estimates. The analysing may further include mapping the time series of non-respiratory-related internal delay estimates to a time series of values of length of the mask tube. The analysing may further include determining whether an increase in the length of the mask tube over many therapy sessions may be greater than a threshold. The analysing may further include determining a variability of the length of the mask tube over a session of respiratory therapy.

Some implementations of the present technology include a device for generating a status indication about a patient interface associated with a respiratory therapy system configured to deliver respiratory therapy to a patient, the respiratory therapy system may include a flow generator configured to generate a supply of pressurized air along an air circuit to the patient interface. The device may include a sensor configured to generate a sound signal representing a sound in the air circuit. The device may include a controller. The controller may include one or more processors and a memory. The one or more processors may be configured by program instructions stored in the memory to execute any one or more aspects of the methods described herein.

Some implementations of the present technology include a device for generating a status indication about a patient interface for a respiratory therapy system configured to deliver respiratory therapy to a patient, the respiratory therapy system may include a flow generator configured to generate a supply of pressurized air along an air circuit to the patient interface. The device may include a sensor configured to generate a sound signal representing a sound in the air circuit. The device may include a controller. The controller may be configured to process the sound signal representing a sound in the air circuit, to obtain cepstrum data. The controller may be configured to separate an acoustic signature from the cepstrum data. The acoustic signature may represent a reflection of sound from the patient interface along the air circuit. The controller may be configured to estimate an internal delay of the acoustic signature. The internal delay may be a delay between two portions of the acoustic signature. Each portion may represent a reflection from a corresponding component of the patient interface separated by a mask tube. The controller may be configured to repeat the processing, separating, and estimating to generate a time series of estimates of the internal delay. The controller may be configured to analyse the time series of internal delay estimates. The controller may be configured to generate one or more output indicators based on the analysing, the one or more output indicators concerning patient interface status.

In some implementations, to analyse the time series, the controller may be configured to filter the time series of internal delay estimates to allow passing of frequencies within a breathing rate frequency band. To analyse the time series, the controller may be further configured to analyse the filtered time series of internal delay estimates to generate an indication of concentration of carbon dioxide in the mask tube. To analyse the time series, the controller may be configured to remove breathing-rate-frequency-band variations from the time series of internal delay estimates to obtain a time series of non-respiratory-related internal delay estimates. To analyse the time series, the controller may be further configured to map the time series of non-respiratory-related internal delay estimates to a time series of values of length of the mask tube. To analyse the time series, the controller may be further configured to determine whether an increase in the length of the mask tube over many therapy sessions may be greater than a threshold. To analyse the time series, the controller may be further configured to determine a variability of the length of the mask tube over a session of respiratory therapy.

Some implementations of the present technology include apparatus that may include means for generating a sound signal representing a sound in an air circuit of a respiratory therapy system, the respiratory therapy system may include a flow generator configured to generate a supply of pressurized air from an outlet along the air circuit to a patient interface. The apparatus may include means for processing the sound signal representing a sound in the air circuit, to obtain cepstrum data. The apparatus may include means for separating an acoustic signature from the cepstrum, the acoustic signature representing a reflection of sound from the patient interface along the air circuit. The apparatus may include means for estimating an internal delay of the acoustic signature, wherein the internal delay may be a delay between two portions of the acoustic signature, each portion representing a reflection from a corresponding component of the patient interface separated by a mask tube. The apparatus may include means for repeating the processing, separating, and estimating to generate a time series of estimates of the internal delay. The apparatus may include means for analysing the time series of internal delay estimates. The apparatus may include means for generating one or more output indicators based on the analysing, the one or more output indicators concerning patient interface status.

Some implementations of the present technology include a respiratory therapy system for delivering respiratory therapy to a patient. The system may include a flow generator configured to generate a supply of pressurized air. The system may include an air circuit connected to the flow generator so as to convey the supply of pressurised air to a patient interface. The system may include a device for generating a patient and/or system status indication with the respiratory therapy system, where the device may include any one or more of the features described herein.

Some implementations of the present technology include a respiratory therapy system for delivering respiratory therapy to a patient. The system may include a flow generator configured to generate a supply of pressurized air. The system may include an air circuit connected to the flow generator so as to convey the supply of pressurised air to a patient interface. The system may include a device for generating a status indication about the patient interface, the device including any one or more of the features described herein.

The methods, systems, devices and apparatus described herein can provide improved functioning in a processor, such as of a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

FIG. 2 shows an overview of a human respiratory system including the nasal and oral cavities, the larynx, vocal folds, oesophagus, trachea, bronchus, lung, alveolar sacs, heart and diaphragm.

4.3 Patient Interface

FIG. 3 shows an example of a patient interface in the form of a nasal mask in accordance with one form of the present technology.

4.4 RPT Device

4.5 Humidifier

Figure 5A:
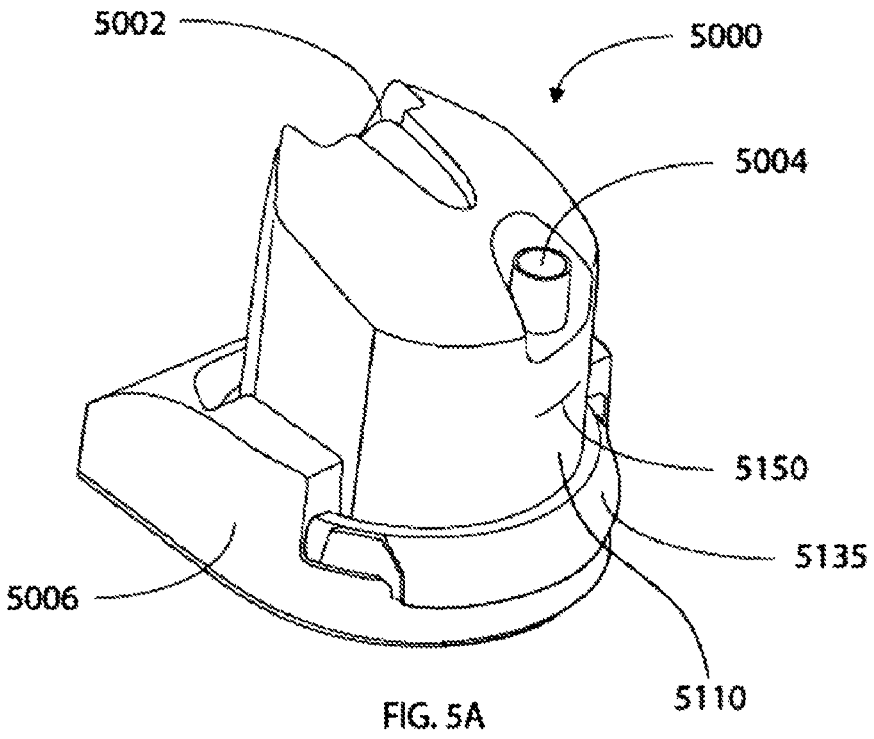

FIG. 5A shows an isometric view of a humidifier in accordance with one form of the present technology.

Figure 5B:
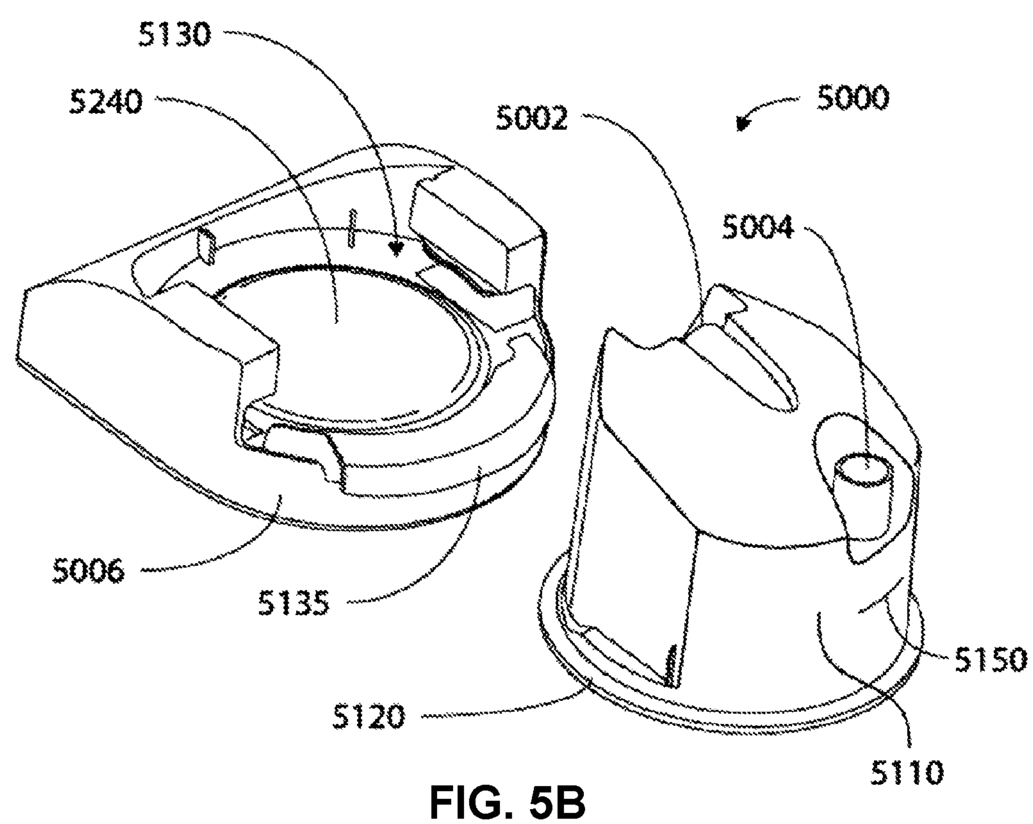

FIG. 5B shows an isometric view of a humidifier in accordance with one form of the present technology, showing a humidifier reservoir 5110 removed from the humidifier reservoir dock 5130.

4.6 Breathing Waveforms

Figure 6:
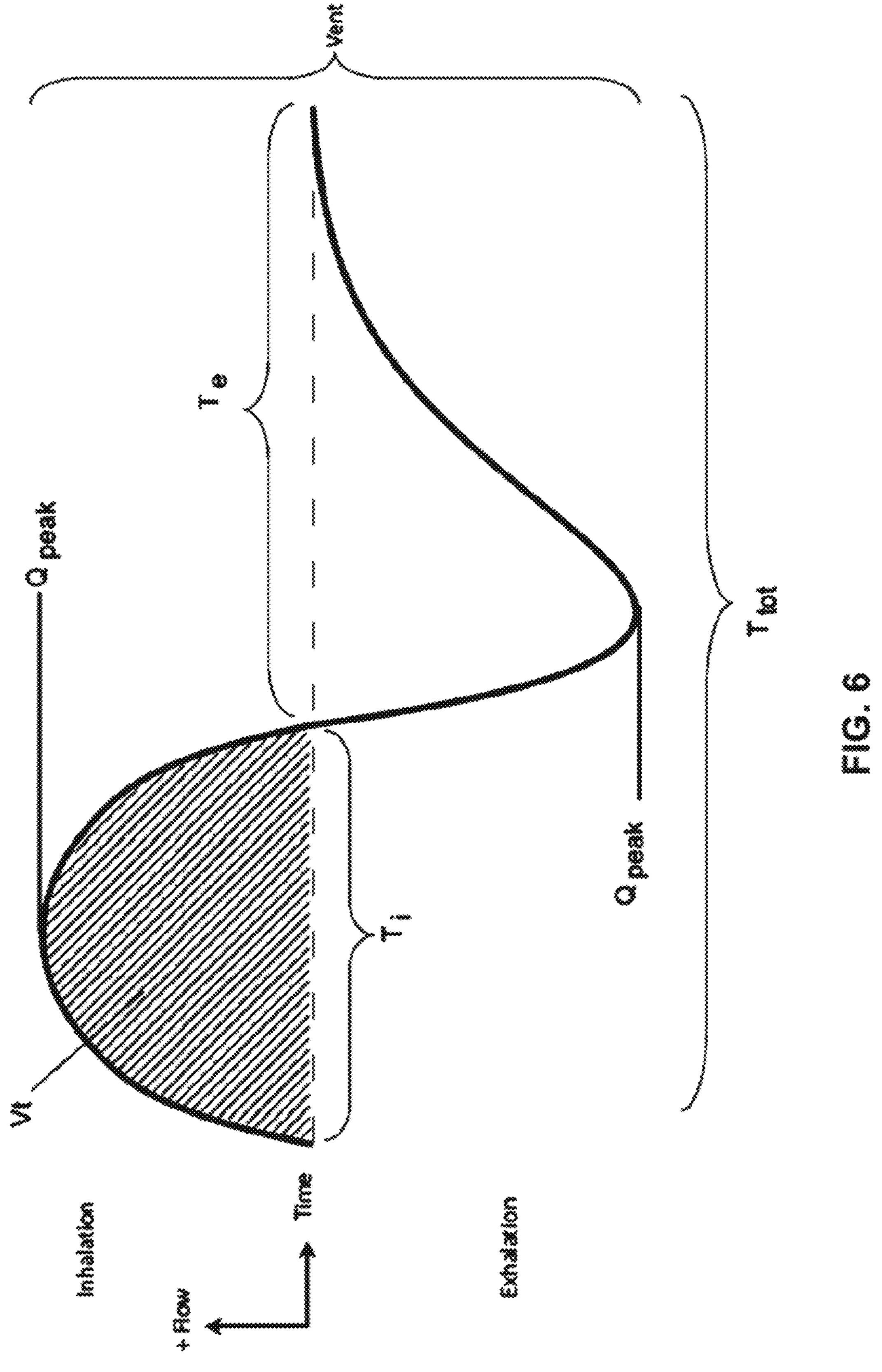

FIG. 6 shows a model typical breath waveform of a person while sleeping. The horizontal axis is time, and the vertical axis is respiratory flow rate. While the parameter values may vary, a typical breath may have the following approximate values: tidal volume, Vt, 0.5 L, inhalation time, Ti, 1.6 s, peak inspiratory flow rate, Qpeak, 0.4 L/s, exhalation time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/min. A typical duty cycle, the ratio of Ti to Ttot, is about 40%.

4.7 Acoustic Analysis

Figure 7:
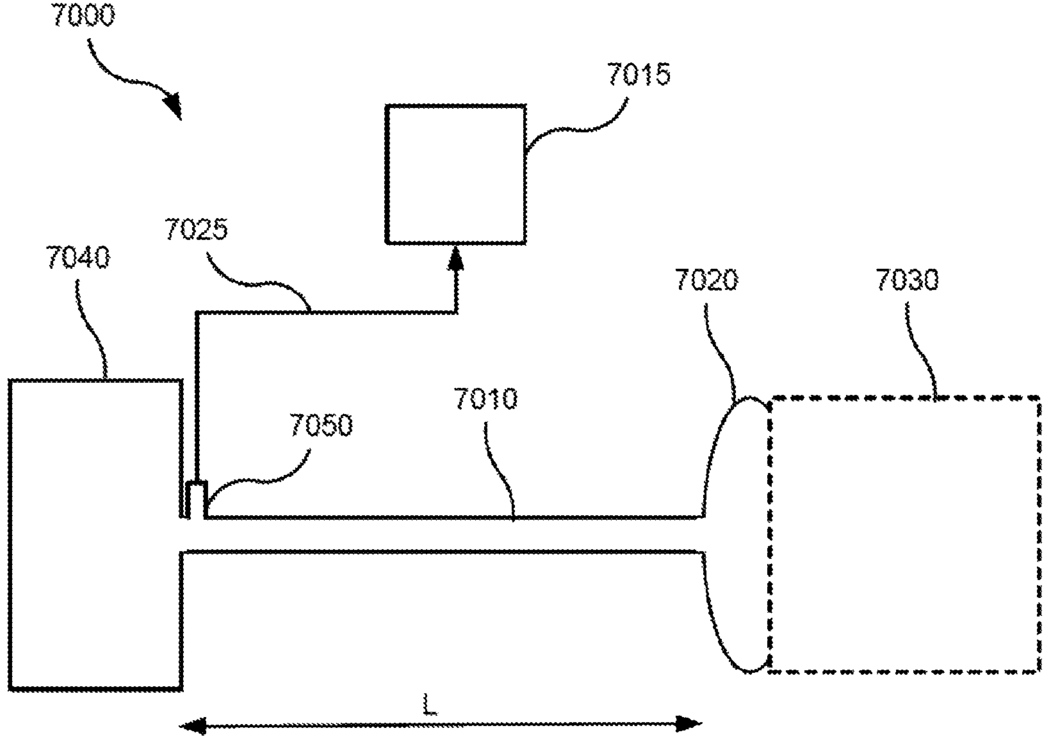

FIG. 7 is a schematic view of a respiratory therapy system in accordance with one example of the present technology that may include acoustic analysis apparatus as described in more detail herein.

Figure 8:
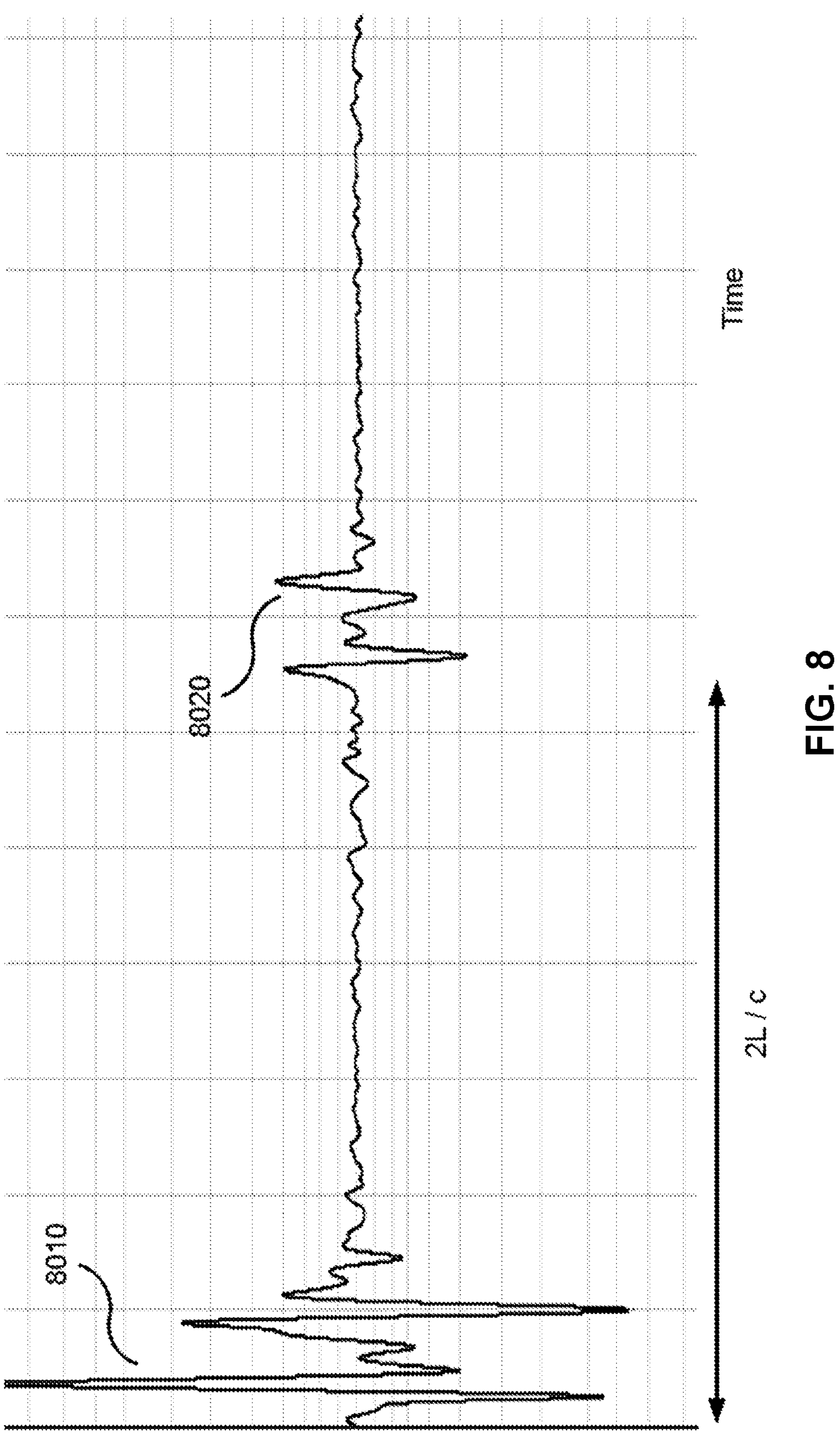
Figure 9:
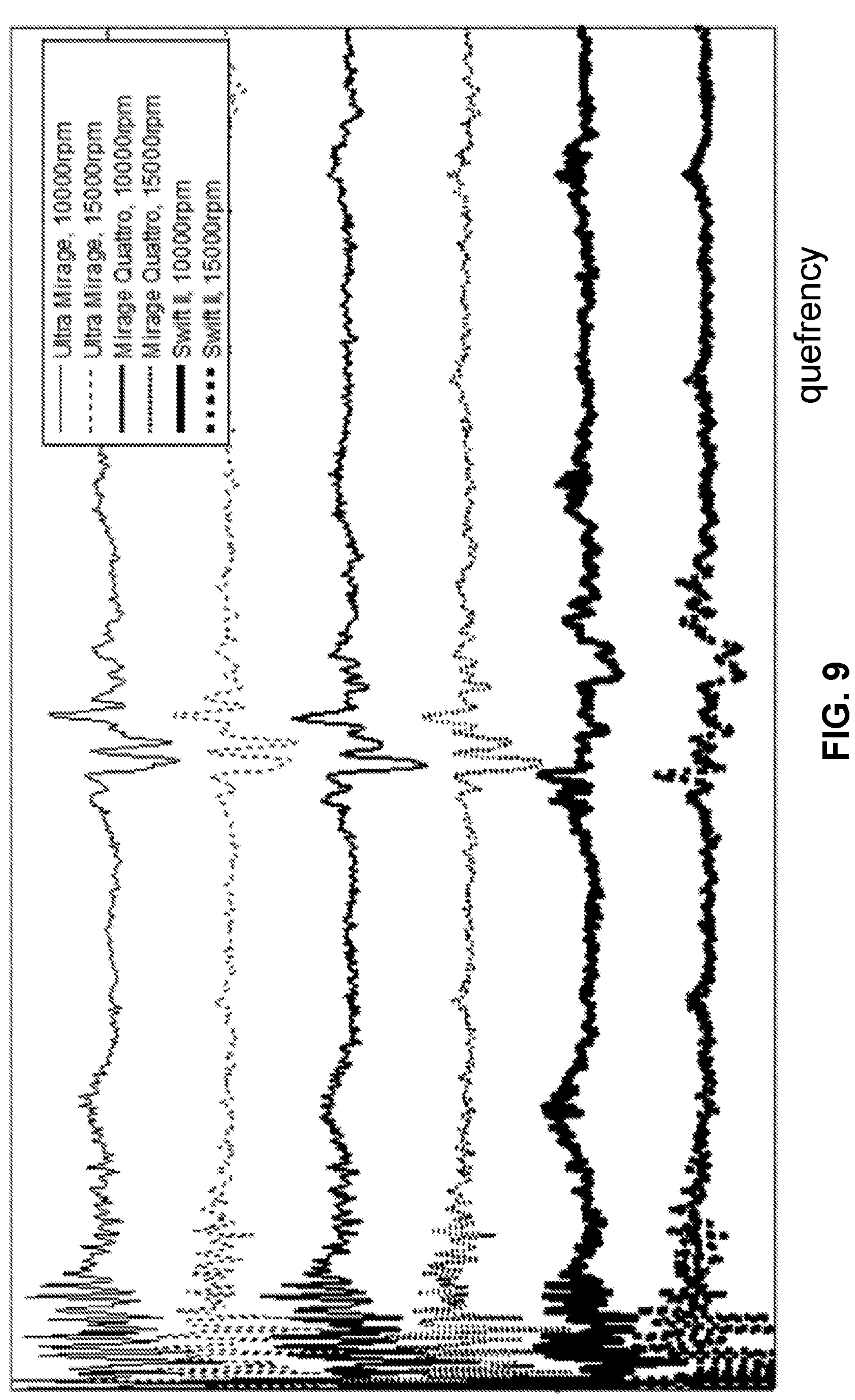
Figure 10:
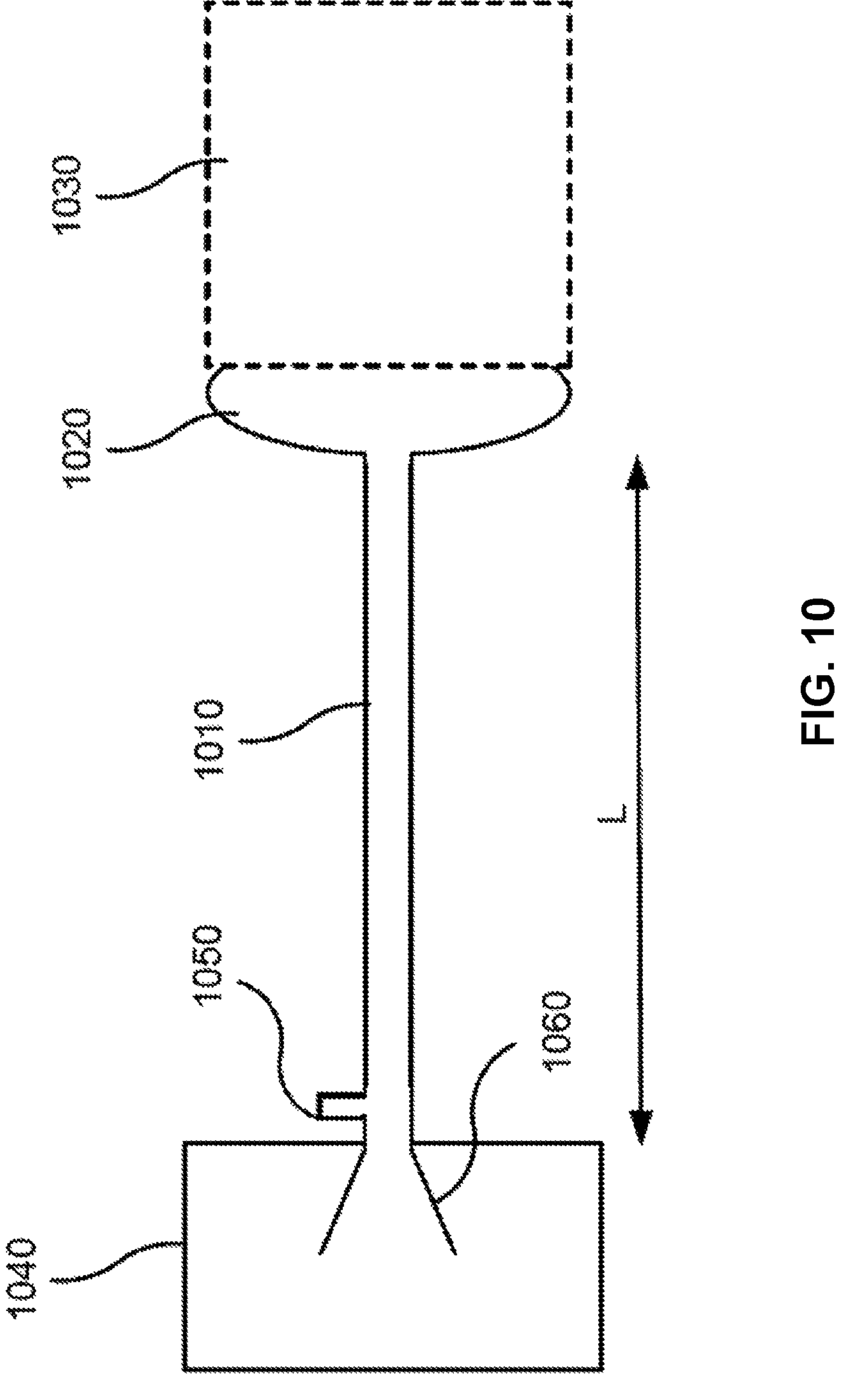

FIG. 8 is a graph containing an example of an Impulse Response Function of the respiratory therapy system of FIG. 7;

FIG. 9 is a graph containing cepstra concerning various example masks at various blower speeds in the respiratory therapy system of FIG. 7;

FIG. 10 is a schematic view of a respiratory therapy system in accordance with an example aspect of the present technology.

Figure 11:
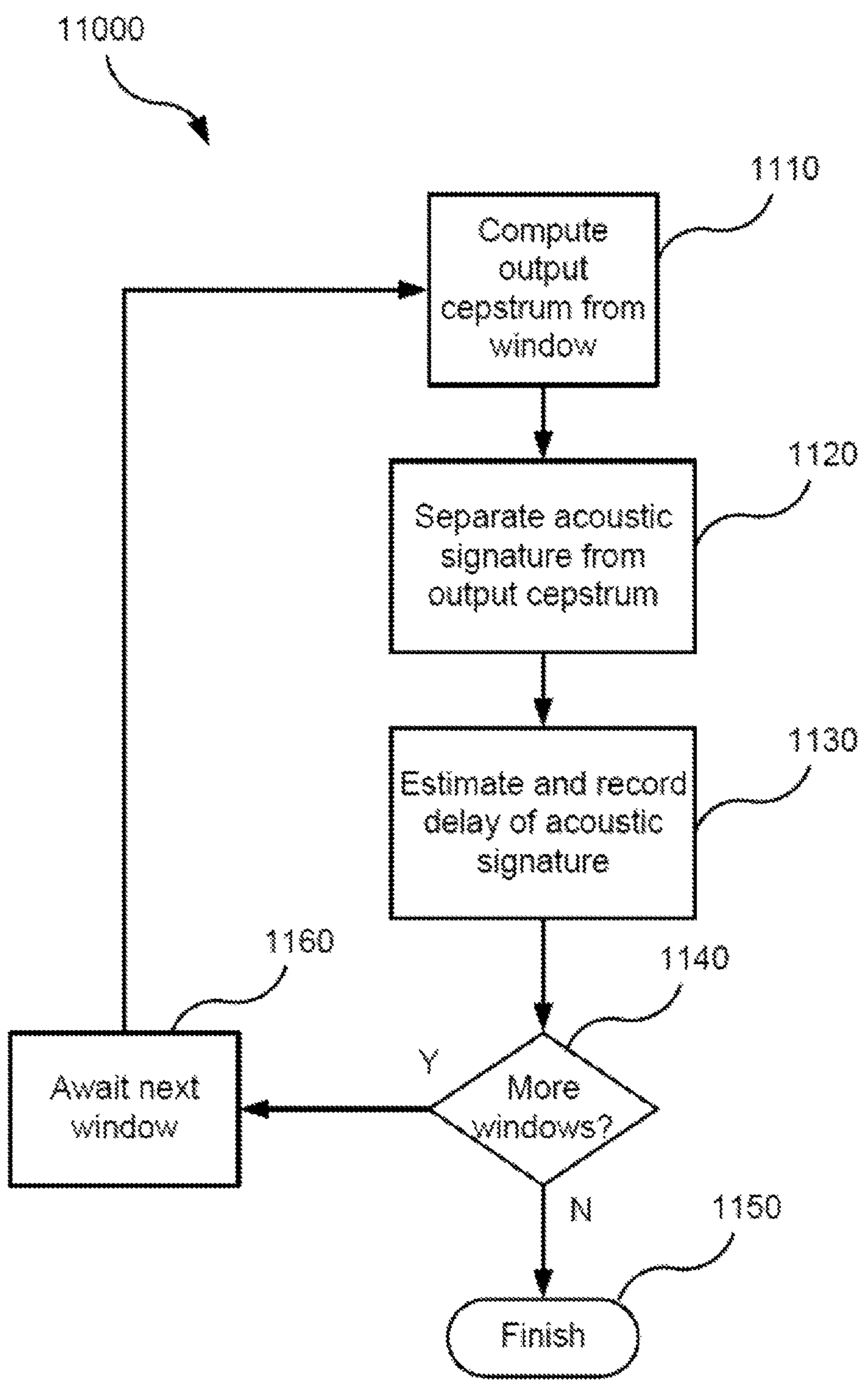

FIG. 11 is a flow chart illustrating a method of estimating an acoustic signature delay of the air circuit of the respiratory therapy system of FIG. 7 in accordance with an example of the present technology.

Figure 12:
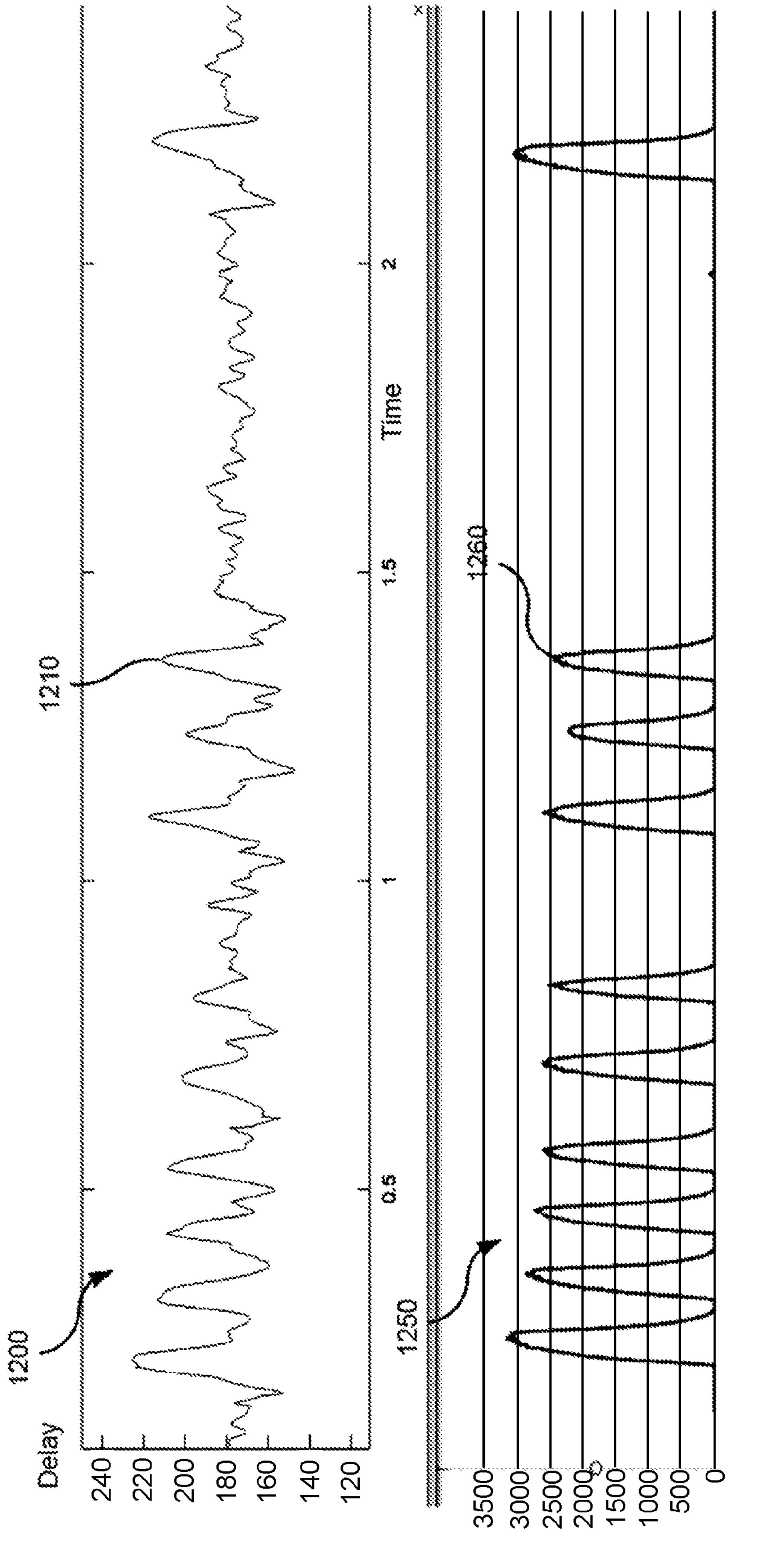

FIG. 12 contains two contemporaneous time series plotted on the same time axis: acoustic signature delay (top trace), and measured carbon dioxide concentration (bottom trace) in a conduit of the respiratory therapy system of FIG. 7.

Figure 13:
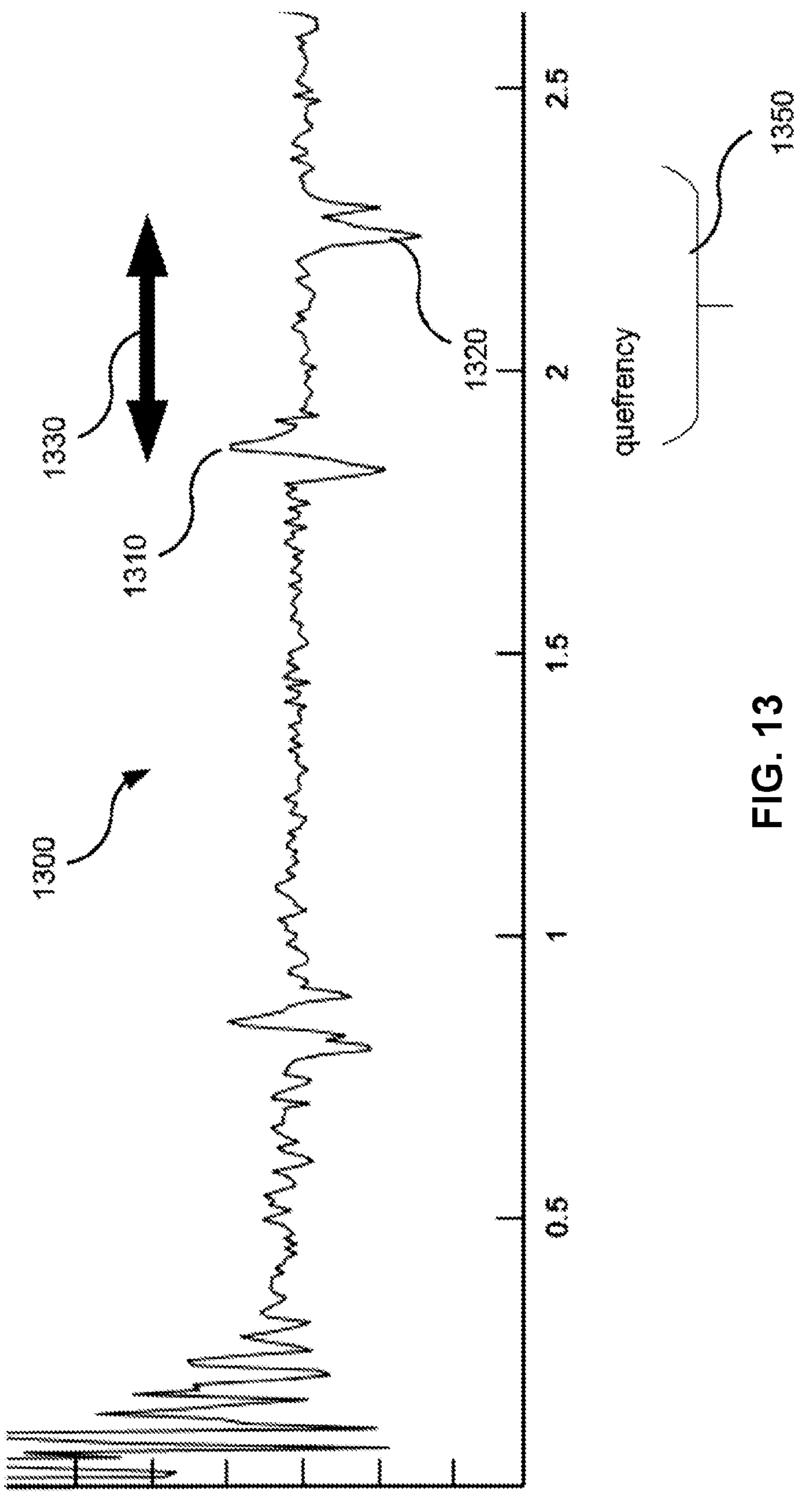

FIG. 13 is a graph containing a cepstrum concerning a pillows mask including a mask tube in the respiratory therapy system of FIG. 7.

Figure 14:
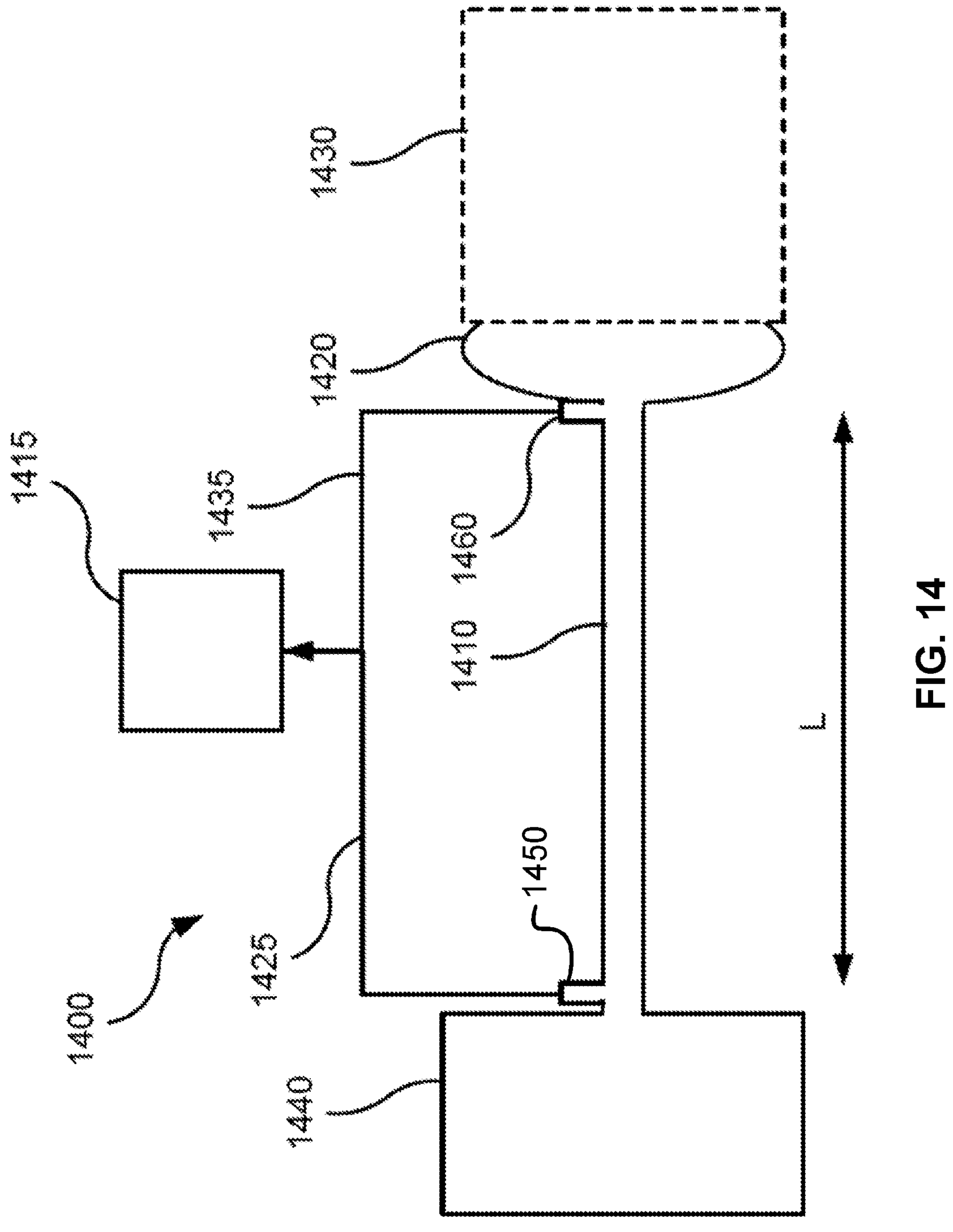

FIG. 14 is a schematic view of a respiratory therapy system in accordance with an example of the present technology that may include acoustic analysis apparatus as described in more detail herein.

Figure 15:
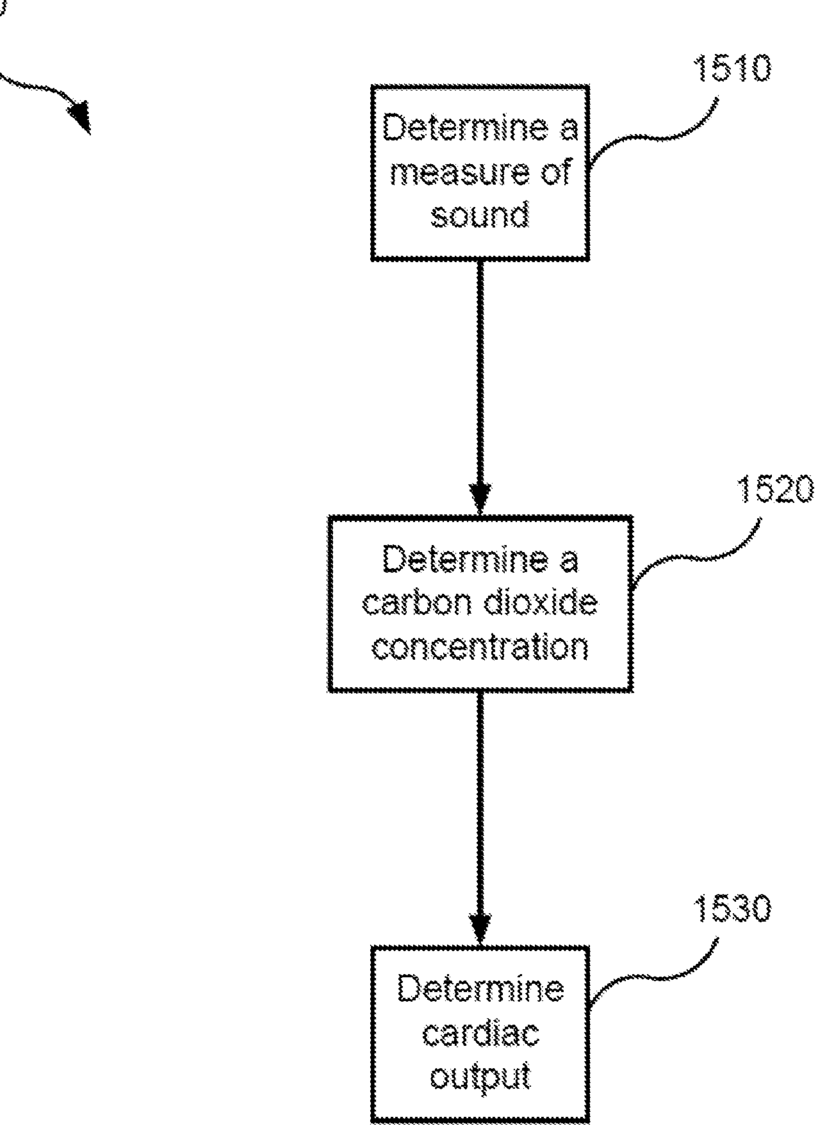

FIG. 15 is a flow chart illustrating an example process for determining the cardiac output of a patient in accordance with one aspect of the present technology.

Figure 16:
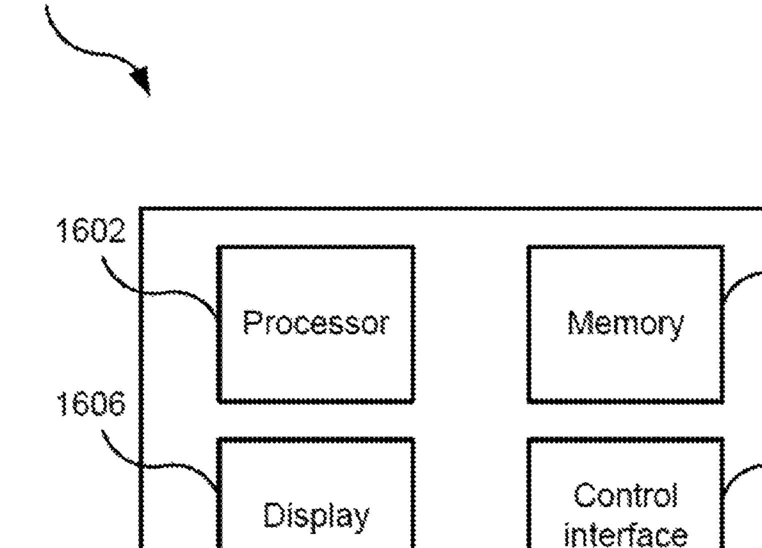

FIG. 16 is a diagram of example components of an implementation of the acoustic analysis apparatus, such as of FIG. 7 or FIG. 14, according to one aspect of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

In the present specification, "identification" of a component means identification of the type of that component. In the present specification, "mask" is used synonymously with "patient interface" for brevity, even though there exist patient interfaces that are not usually described as "masks".

5.1 THERAPY

In one form, the present technology comprises a method for treating a respiratory disorder comprising the step of applying positive pressure to the entrance of the airways of a patient 1000.

5.2 THERAPY SYSTEMS

In one form, the present technology comprises a system for treating a respiratory disorder. The respiratory therapy (RT) system may comprise an RPT device 4000 and a humidifier 5000 for delivering a supply of humidified air at positive pressure to the patient 1000 via an airpath comprising an air circuit 4170 and a patient interface 3000.

5.3 PATIENT INTERFACE

Figure 1A:
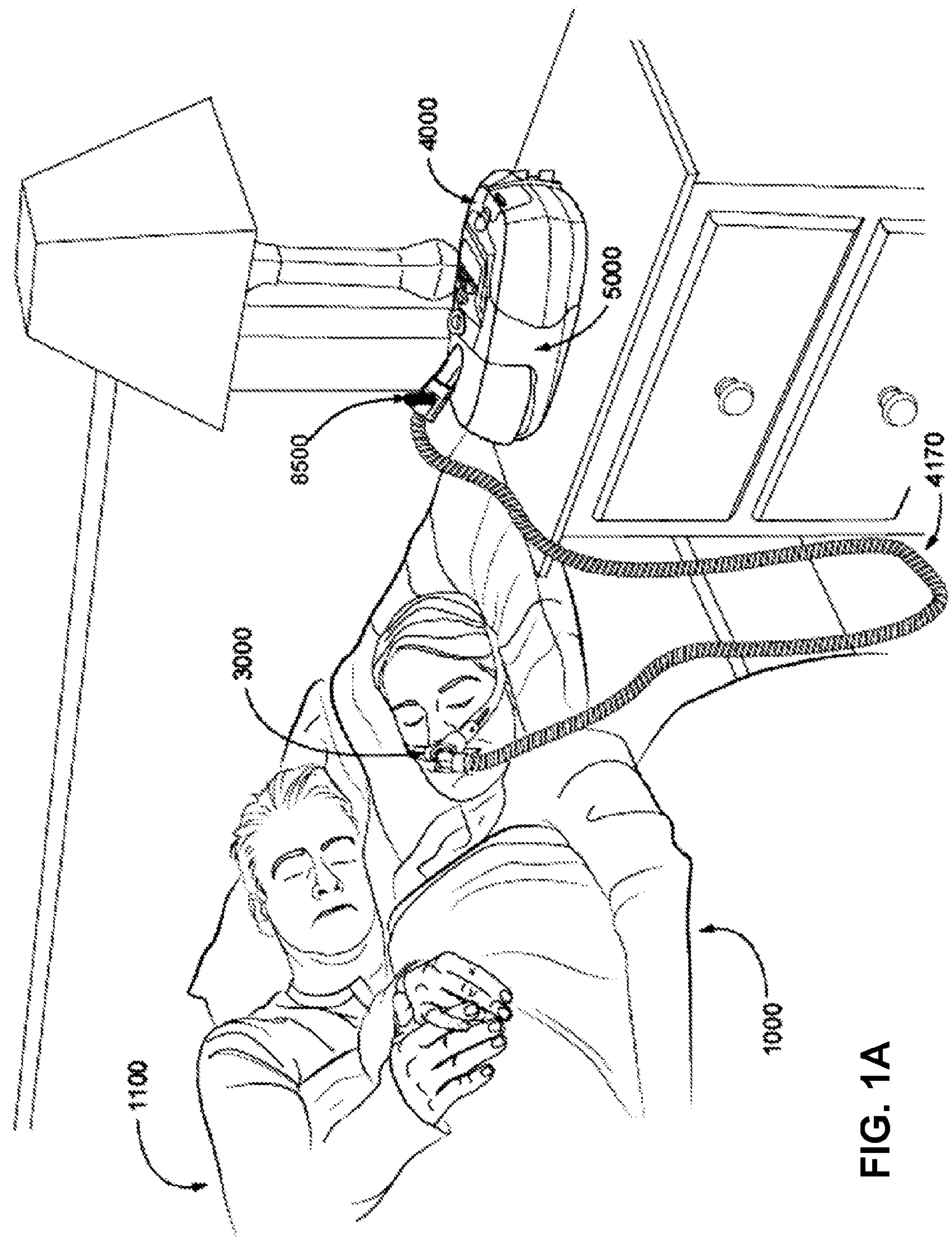
Figure 1B:
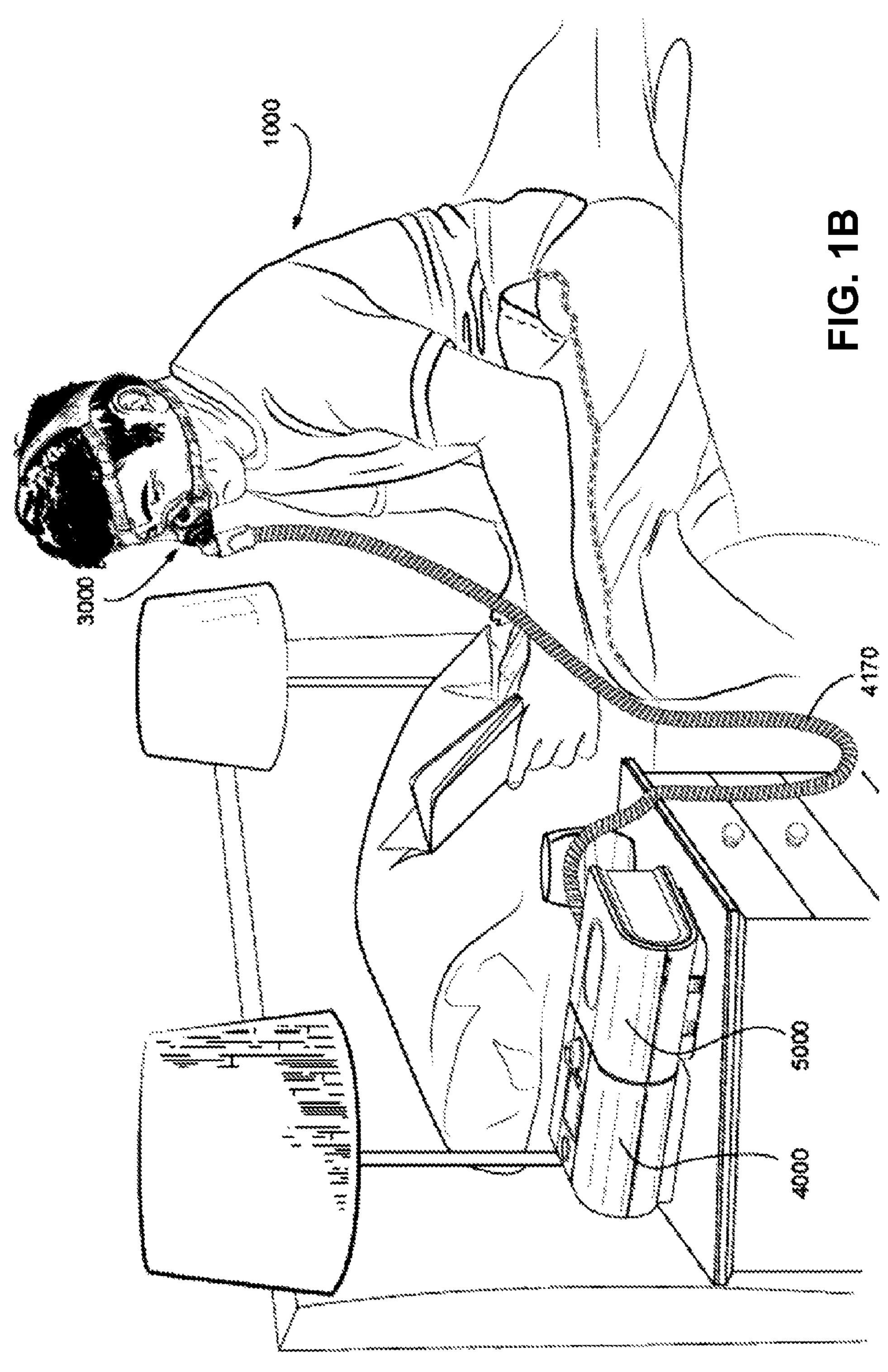
Figure 1C:
Figure 2:
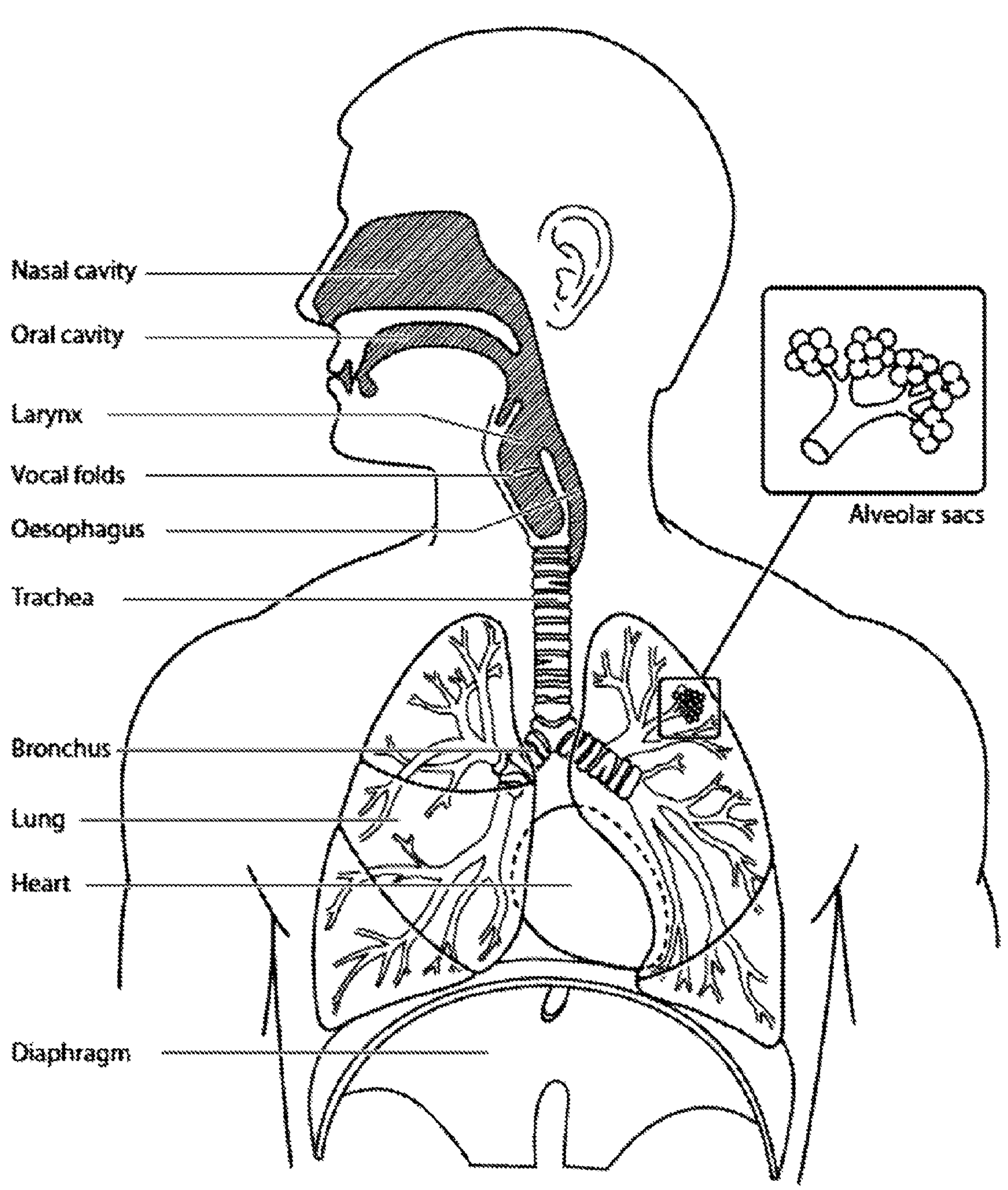
Figure 3:
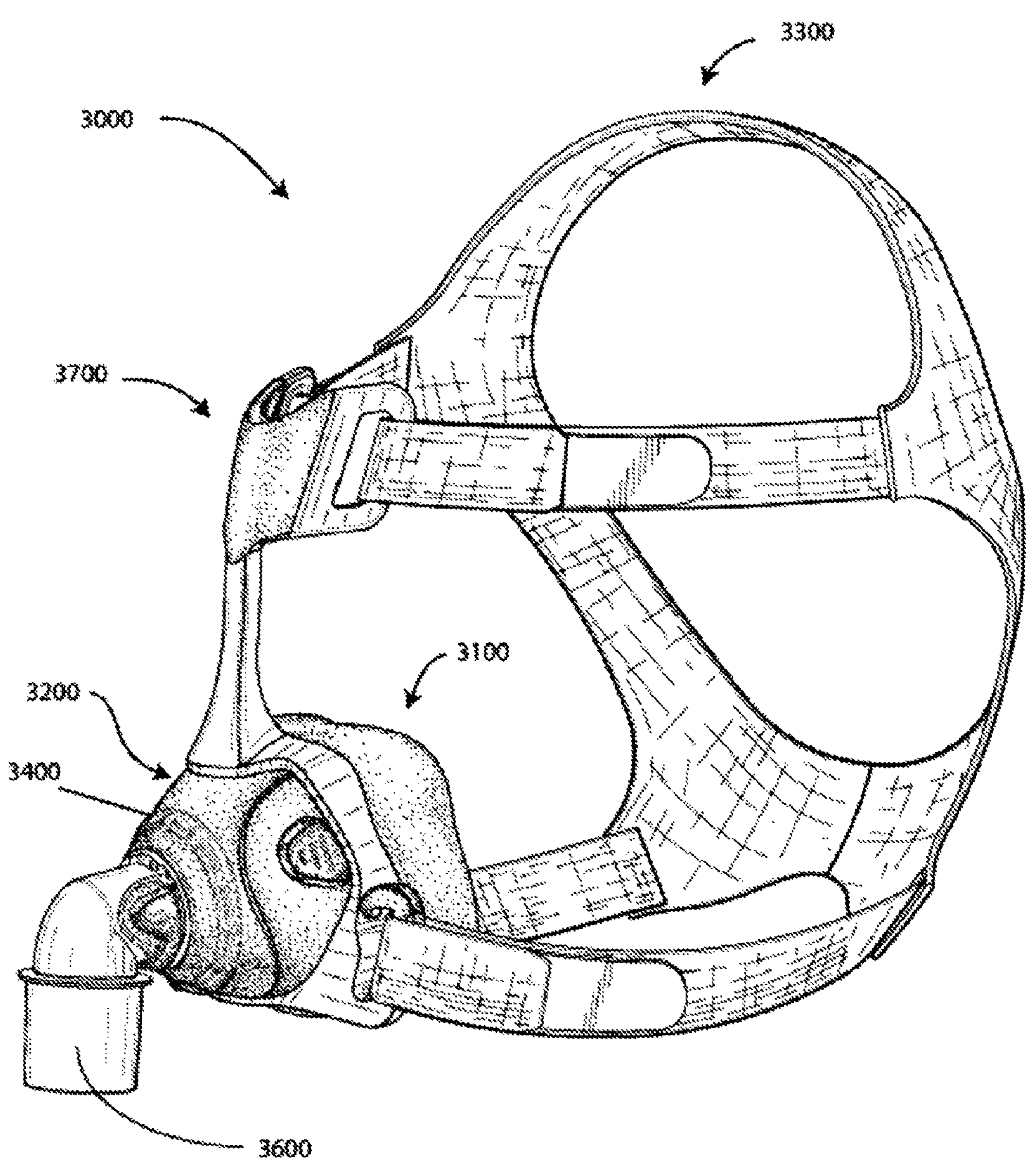

An example non-invasive patient interface 3000 is shown in FIG. 3 and comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

The patient interface 3000 in accordance with one form of the present technology is constructed and arranged to be able to provide a supply of air at a positive pressure, such as of at least 4 $cmH_2O$, or at least 10 $cmH_2O$, or at least 20 $cmH_2O$, or at least 25 $cmH_2O$ with respect to ambient.

5.3.1 Seal-Forming Structure

In one form of the present technology, a seal-forming structure 3100 provides a target seal-forming surface region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

5.3.3 Positioning and Stabilising Structure

The seal-forming structure 3100 of the patient interface 3000 of the present technology may be held in sealing position in use by the positioning and stabilising structure 3300, such as headgear.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled carbon dioxide by the patient while maintaining the therapeutic pressure in the plenum chamber in use. One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.3.5 Connection Port

Connection port 3600 allows for connection of the patient interface 3000 to the air circuit 4170.

In some implementations, there may be a length of flexible tube (not illustrated) separating the plenum chamber 3200 and the connection port 3600. Such a length of tube is referred to herein as the "mask tube" to distinguish it from the conduit or tube making up the air circuit 4170.

5.4 RPT DEVICE

Figure 4A:
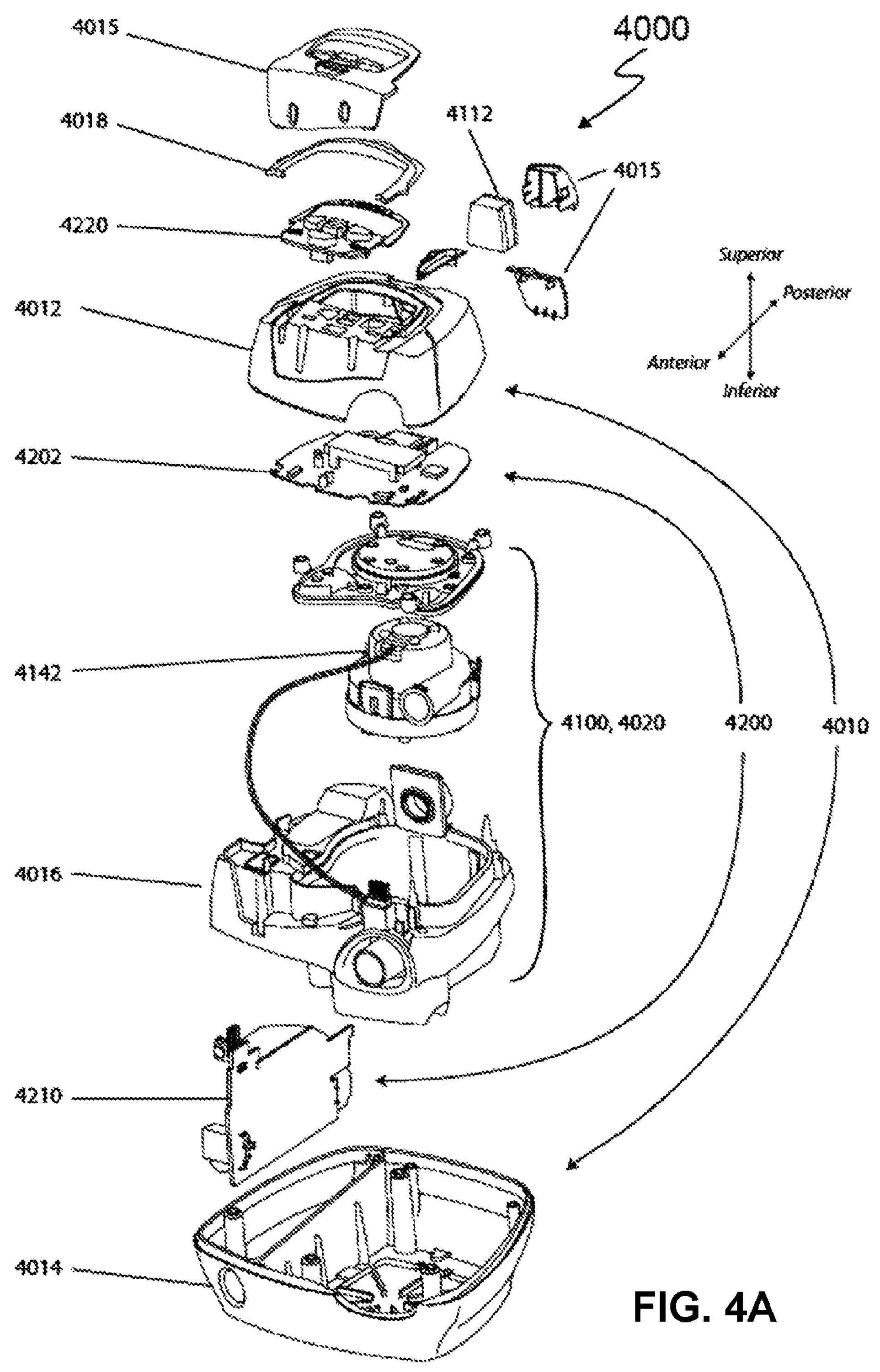
FIG. 4A shows an exploded view of an example respiratory pressure therapy (RPT) device 4000 in accordance with one form of the present technology.
Figure 4B:
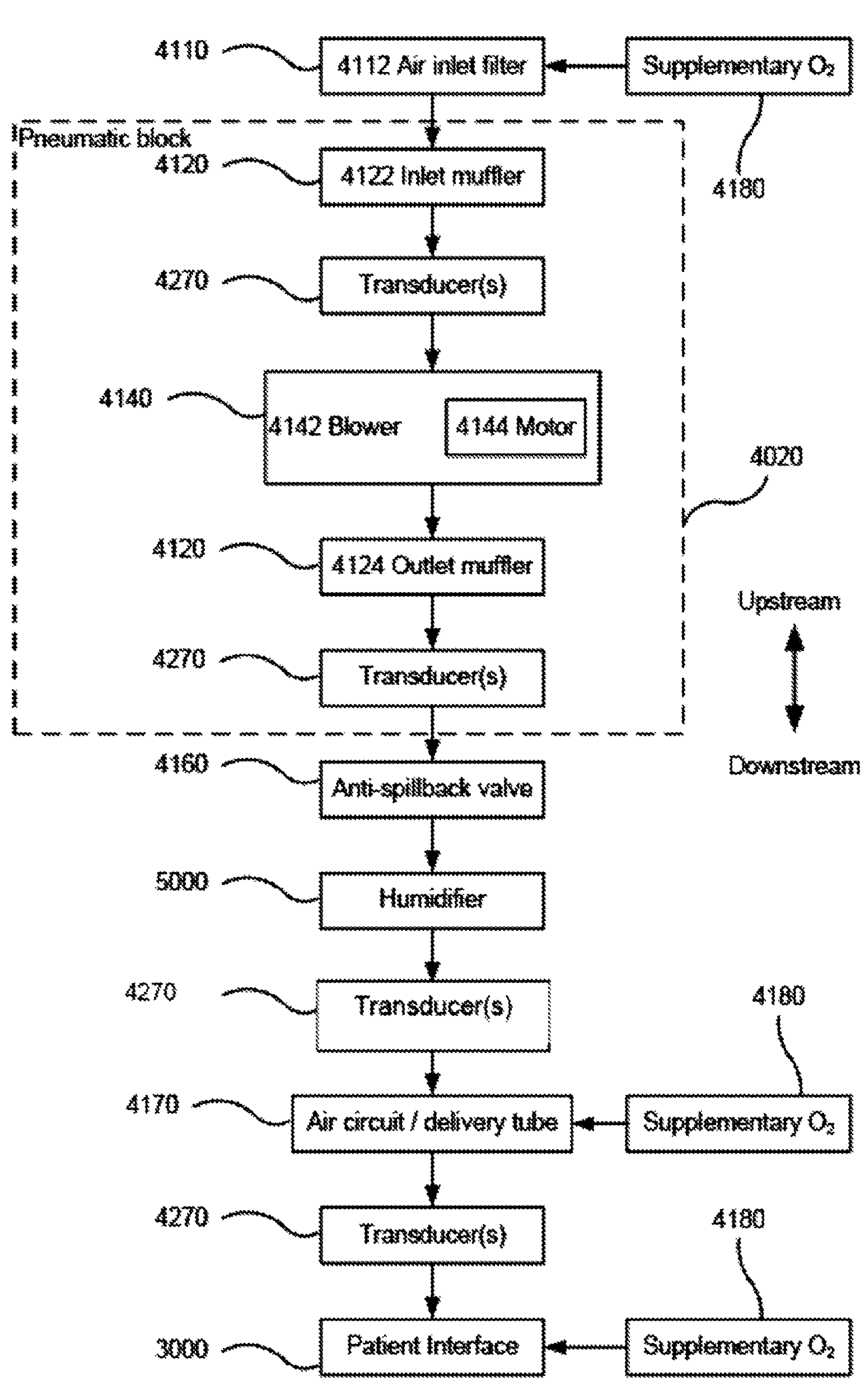
FIG. 4B is a schematic diagram of the pneumatic path of an RPT device in accordance with one form of the present technology. The directions of upstream and downstream are indicated.

A respiratory pressure therapy (RPT) device 4000 in accordance with one aspect of the present technology is shown in exploded view in FIG. 4A and comprises mechanical, pneumatic, and/or electrical components and is configured to execute one or more algorithms 4300. The RPT device 4000 may be configured to generate a flow of air for delivery to a patient's airways, such as to treat one or more of the respiratory conditions described elsewhere in the present document. Although the acoustic technology and methods described herein are generally illustrated in relation to an example RPT device 4000, such technology and methods may similarly be implemented in or with other RT devices, such as in or with HFT device(s).

In one form, the RPT device 4000 is constructed and arranged to be capable of delivering a flow of air in a range of −20 L/min to +150 L/min while maintaining a positive pressure of at least 4 $cmH_2O$, or at least 10 $cmH_2O$, or at least 20 $cmH_2O$, or at least 25 $cmH_2O$.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more airpath items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors and flow rate sensors.

One or more of the airpath items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Pressure Generator

In one form of the present technology, a pressure generator 4140 for producing a downstream air flow such as a flow, or a supply, of air at positive pressure is a controllable blower 4142. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,14; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.2 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions or processor control instructions expressing the one or more methodologies described herein, such as the one or more algorithms 4300.

5.4.1.3 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile computing device such as a smartphone or tablet device, or a remote control.

5.4.2 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules.

5.5 HUMIDIFIER 5.5.1 Humidifier Overview

In one form of the present technology the RT system comprises a humidifier 5000 between the RPT device 4000 and the air circuit 4170 (as shown in FIG. 4A) to change the absolute humidity of air for delivery to a patient relative to that of ambient air. Typically, the humidifier 5000 is used to increase the absolute humidity and increase the temperature of the flow of air (relative to ambient air) before delivery to the patient's airways.

The humidifier 5000 (e.g. as shown in FIG. 5A) may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.5.2 Humidifier Components 5.5.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.5.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.5.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.5.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.5.2.5 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller 5250.

5.6 AIR CIRCUIT

An air circuit 4170 in accordance with an aspect of the present technology is a conduit or a tube constructed and arranged to allow, in use, a pressurised flow of air to travel between two components such as the humidifier 5000 and the patient interface 3000.

In particular, the air circuit 4170 may be in fluid communication with the outlet 5004 of the humidifier 5000 and the connection port 3600 of the patient interface 3000.

5.7 TRANSDUCER(S)

An RT system may comprise one or more transducers (sensors) 4270 configured to measure one or more of any number of parameters in relation to an RT system, its patient, and/or its environment. A transducer may be configured to produce an output signal representative of the one or more parameters that the transducer is configured to measure.

The output signal may be one or more of an electrical signal, a magnetic signal, a mechanical signal, a visual signal, an optical signal, a sound signal, or any number of others which are known in the art.

A transducer may be integrated with another component of an RT system, where one exemplary arrangement would be the transducer being internal of an RPT device. A transducer may be substantially a 'standalone' component of an RT system, an exemplary arrangement of which would be the transducer being external to the RPT device.

A transducer may be configured to communicate its output signal to one or more components of an RT system, such as an RPT device, a local external device, or a remote external device. External transducers may be for example located on a patient interface, or in an external computing device, such as a smartphone. External transducers may be located for example on or form part of the air circuit, e.g., the patient interface.

The one or more transducers 4270 may be constructed and arranged to generate signals representing properties of air such as a flow rate, a pressure or a temperature. The air may be a flow of air from the RT device to a patient, a flow of air from the patient to the atmosphere, ambient air or any others. The signals may be representative of properties of the flow of air at a particular point, such as the flow rate of air in the airpath between the RT device and the patient. In one form of the present technology, one or more transducers 4270 are located in a pneumatic path of the RT device, such as downstream of the humidifier 5000.

5.7.1 Pressure Sensor

In accordance with one aspect of the present technology, the one or more transducers 4270 comprises a pressure sensor located in fluid communication with the pneumatic path of the RT device. An example of a suitable pressure sensor is a transducer from the HONEYWELL ASDX series. An alternative suitable pressure sensor is a transducer from the NPA Series from GENERAL ELECTRIC. In one implementation, the pressure sensor is located in the air circuit 4170 adjacent the outlet 5004 of the humidifier 5000.

The pressure sensor (microphone) 4270 is configured to generate a sound signal representing the variation of pressure within the air circuit 4170. The microphone 4270 may be directly exposed to the flow of air in the air circuit 4170 for greater sensitivity to sound, or may be encapsulated behind a thin layer of flexible membrane material. This membrane may function to protect the microphone 4270 from heat and/or humidity.

The sound signal from the microphone 4270 may be received by the central controller 4230, serving as acoustic analysis apparatus, for acoustic processing and analysis according to one or more of the algorithms/methods described herein and below. Alternatively, the sound signal from the microphone 4270 may be received by other acoustic analysis apparatus for acoustic processing and analysis according to one or more of the algorithms/methods described herein and below.

5.8 ACOUSTIC ANALYSIS

According to one or more aspects of the present technology, acoustic analysis may be implemented, such as by apparatus described herein, to determine one or more parameters in relation to respiratory disorders, or systems for treatment of respiratory disorders.

Acoustic analysis according to aspects of the present technology may have one or more advantages over the prior art, such as reducing cost of care, delivering higher quality of therapy, improving ease of use of a therapy system, reducing waste, and providing digital connectivity at a low cost.

As will be clear in the context of the remainder of the document, the terms 'acoustic', 'sound', or 'noise' in the present document are generally intended to include airborne vibrations, regardless of whether they may be audible or inaudible. As such, the terms 'acoustic', 'sound', or 'noise' in the present document are intended to include airborne vibrations in the ultrasonic, or subsonic ranges, unless specifically stated otherwise.

Some implementations of the disclosed acoustic analysis technologies may implement cepstrum analysis. A cepstrum may be considered the inverse Fourier Transform of the logarithm of the forward Fourier Transform of the signal.

The operation essentially can convert a convolution of an impulse response function (IRF) and an input sound signal into an addition operation so that the input sound signal may then be more easily accounted for or removed so as to isolate data of the IRF for analysis. Techniques of cepstrum analysis are described in detail in a scientific paper entitled "The Cepstrum: A Guide to Processing" (Childers et al, Proceedings of the IEEE, Vol. 65, No. 10, October 1977) and Randall R B, *Frequency Analysis*, Copenhagen: Bruel & Kjaer, p. 344 (1977, revised ed. 1987). The application of cepstrum analysis to respiratory therapy system airpath characteristic detection is described in detail in PCT publication no. WO2010/091462, titled "Acoustic Detection for Respiratory Treatment Apparatus", the entire contents of which are hereby incorporated by reference.

Cepstrum analysis may be understood in terms of the property of convolution. The convolution of $f$ and g can be written as $f*g$. This operation may be the integral of the product of the two functions ($f$ and g) after one is reversed and shifted. As such, it is a type of integral transform as follows:

$$(f*g)(t) @ \int_{-\infty}^{\infty} f(\tau)g(t-\tau)d\tau \tag{1}$$

While the symbol t is used above, it need not represent the time domain. But in that context, the convolution formula can be described as a weighted average of the function $f(T)$ at the moment t where the weighting is given by $g(-\tau)$ simply shifted by amount t. As t changes, the weighting function emphasizes different parts of the input function.

A mathematical model that can relate output to the input for a time-invariant linear acoustic system, such as the airpath of a respiratory therapy system, can be based on convolution. The sound signal generated by a microphone 4270 adapted to sense sound in the air circuit 4170 may be considered as an input (sound) signal "convolved" with the system Impulse Response Function (IRF) as a function of time (t).

$$y(t) = s_1(t) * h_1(t) \tag{2}$$

where y(t) is the output (sound) signal generated by the microphone 4270; $s_1(t)$ is the input signal representing sound (e.g., motor operation noise) generated in or by a pressure generator 4140 of a respiratory therapy device 4000, and $h_1(t)$ is the system IRF from the source of the sound to the microphone 4270. The system IRF $h_1(t)$ may be thought of as the system response to a unit impulse input. In a linear acoustic system such as the airpath of a respiratory therapy system, the system IRF $h_1(t)$ consists of reflections of the unit impulse from any discontinuities in the airpath such as junctions between two components.

Conversion of Equation (2) into the frequency domain by means of the Fourier Transform of the sound signal y(t) (e.g., a discrete Fourier Transform ("DFT") or a fast Fourier transform ("FFT")) and considering the Convolution Theorem, the following equation is produced:

$$Y(f) = S_1(f)H_1(f) \tag{3}$$

where $Y(f)$ is the Fourier Transform (spectrum) of y(t); $S_1(f)$ is the Fourier Transform of $s_1(t)$; and $H_1(f)$ is the Fourier Transform of $h_1(t)$. In other words, a convolution in the time domain becomes a multiplication in the frequency domain.

A logarithm operation may be applied to Equation (3) so that the multiplication is converted into an addition:

$$\text{Log}\{Y(f)\} = \text{Log}\{S_1(f)\} + \text{Log}\{H_1(f)\} \tag{4}$$

Equation (4) may then be converted back into the time domain, by an Inverse Fourier Transform (IFT) (e.g., an inverse DFT or inverse FFT), which results in a complex-valued "Cepstrum"—the inverse Fourier Transform of the logarithm of the spectrum $Y(f)$:

$$\begin{aligned} \tilde{Y}(\tau) &= IFT[\text{Log}\{Y(f)\}] \\ &= IFT[\text{Log}\{S_1(f)\}] + IFT[\text{Log}\{H_1(f)\}] \\ &= \tilde{S}_1(\tau) + \tilde{H}_1(\tau) \end{aligned} \tag{5}$$

The abscissa $\tau$ is a real-valued variable known as quefrency, with units measured in seconds. Effects that are convolutive in the time domain thus become additive in the logarithm of the spectrum, and remain so in the cepstrum or quefrency domain. In particular, the output cepstrum $\tilde{Y}(\tau)$ consists of two additive components: the cepstrum $\tilde{S}_1(\tau)$ of the input signal $s_1(t)$, and the cepstrum $\widetilde{H_1}(\tau)$ of the system IRF $h_1(t)$.

Consideration of the data from a cepstrum analysis, such as examining the data values in the quefrency domain, may provide information about the RT system. For example, by comparing cepstrum data of a system from a prior or known baseline of cepstrum data for the system, the comparison, such as a difference, can be used to recognize differences or similarities in the system that may then be used to implement automated control for varying functions or purposes.

5.8.1 Acoustic Signature Extraction

One implementation of the present technology comprises a device, an apparatus, and/or a method for extracting the acoustic signature of a component such as a mask in a respiratory therapy system. The implementation may utilise analysis of a sound signal generated by a sound sensor such as microphone 4270 located as described above.

The technology includes an analysis method that enables the separation of the acoustic mask reflections from the other system noises and responses, including but not limited to blower sound.

An example method of extracting the acoustic signature of a mask is to sample the output signal y(t) generated by the microphone 4270 at a desired sampling rate, such as at least the Nyquist rate, for example 20 kHz. The cepstrum $\tilde{Y}(\tau)$ may be computed from the sampled output signal. A reflection component of the cepstrum may then be separated from the input signal component of the cepstrum. The reflection component of the cepstrum comprises the acoustic reflection from the mask of the input signal, and is therefore referred to as the "acoustic signature" of the mask. The acoustic signature may then be compared with a predefined or predetermined database, such as any suitable type of data storage structure, of previously measured acoustic signatures obtained from systems containing known masks to identify the mask from its acoustic signature. Optionally, some criteria may be set to determine appropriate similarity. In one example embodiment, the comparisons may be completed based on the single largest data peak in the cross-correlation between the measured and stored acoustic signatures. However, this approach may be improved by comparisons over several data peaks or alternatively, wherein the comparisons are completed on extracted unique sets of cepstrum features.

FIG. 7 is a schematic view of an RT system 7000 according to one aspect of the present technology. In this example embodiment as shown in FIG. 7, the conduit 7010 (of length L) effectively acts as an acoustic waveguide for sound produced by the RPT device 7040 (which may include a humidifier), such as including sound from a speaker, or alternatively only noise of the operation of the blower (e.g., motor and/or impeller). In this example embodiment the input signal is sound emitted by the RPT device/humidifier 7040 (i.e. without requiring or using sound from a speaker). The input signal (e.g. an impulse) enters the microphone 7050 positioned at one end of the conduit 7010, travels along the conduit 7010 to mask 7020 and is reflected back along the conduit 7010 by features in the airpath (which includes the conduit and the mask) to enter the microphone 7050 once more. The system IRF (the output signal produced by an input impulse) therefore contains an input signal component and a reflection component. A key feature of the RT system 7000 is the time taken by sound to travel from one end of the airpath to the opposite end. This interval is manifested in the system IRF because the microphone 7050 receives the input signal coming from the RPT device/humidifier 7040, and then some time later receives the input signal filtered by the conduit 7010 and reflected and filtered by the mask 7020 (and potentially any other system 7030 attached to the mask, e.g. a human respiratory system when the mask 7020 is seated on a patient). This means that the component of the system IRF associated with the reflection from the mask end of the conduit 7010 (the reflection component) is delayed in relation to the component of the system IRF associated with the input signal (the input signal component), which arrives at the microphone after a relatively brief delay. (For practical purposes, this brief delay may be ignored and zero time approximated to be when the microphone 7050 first responds to the input signal.) The delay of the reflection component is equal to 2L/c (wherein L is the length of the conduit, and c is the speed of sound in the conduit).

The system 7000 includes an acoustic analysis apparatus 7015 that is in communication with the microphone 7050 via a connection 7025. For example, the acoustic analysis apparatus may include an input interface to receive the signal from the microphone. As described in further detail below, the acoustic analysis apparatus 7015 includes one or more processors configured to implement particular methodologies for determining the concentration of carbon dioxide within the conduit 7010 and subsequently the cardiac output of the patient from the carbon dioxide concentration. Thus, the acoustic analysis apparatus 7015 may include integrated chips, a memory and/or other control instruction, data or information storage medium for performing the methodologies. For example, programmed instructions encompassing such a detection methodology may be coded on integrated chips in the memory of the acoustic analysis apparatus 7015. Such instructions may also or alternatively be loaded as software or firmware using an appropriate non-transient data storage medium.

Another feature of the RT system 7000 is that because the airpath is loss-prone, provided the conduit is long enough, the input signal component decays to a negligible amount by the time the reflection component of the system IRF has begun. If this is the case, then the input signal component may be separated from the reflection component of the system IRF. As an example, FIG. 8 shows an example of one such system IRF from an example therapy system in which the input signal which may originate from the blower 4142 of the RPT device. Alternatively, the input signal may include sound originating from a speaker at the device end of the airpath (with or without sound generated by the RPT device/humidifier 7040). FIG. 8 shows that the reflection component 8020 of the system IRF appears delayed from the input signal component 8010 in the system IRF, with a delay equal to 2L/c.

The cepstrum $\widetilde{H_l}(\tau)$ of the system IRF associated with equations (2), (4), and (5) previously described has generally the same the properties as the system IRF $h_1(t)$. That is, the cepstrum $\widetilde{H_l}(\tau)$ comprises a reflection component concentrated around a quefrency of 2L/c as well as an input signal component concentrated around quefrency zero. In the present technology, the cepstrum analysis is configured to separate the reflection component of the output cepstrum $\tilde{Y}(\tau)$ from other system artefacts (including but not limited to the input signal component $\tilde{S}_1(\tau)$), e.g., by examination of the position and amplitude of the output cepstrum data.

This separation may be accomplished if the input signal $s_1(t)$ is either transient (e.g. an impulse), or stationary random. In either case, the input signal component $\tilde{S}_1(\tau)$ of the cepstrum will be concentrated around a quefrency of zero. For example, the input signal may be the sound produced by an RPT device running at a constant speed during the time period of the microphone's measurement. This sound may be described as "cyclostationary". That is, it is stationary random, and periodic in its statistics. This means that the input signal and the reflection component of the system IRF may be "smeared" across all measured times of the output signal y(t) because at any point in time, the output signal y(t) is a function of all previous values of the input signal and system IRF (see equation (2)). However, the cepstrum analysis described above may be implemented to separate the reflection component of the output cepstrum $\tilde{Y}(\tau)$ from this convolutive mixture.

FIG. 9 depicts the real part of various example cepstra from measurements of a respiratory therapy system, such as the system of FIG. 7, implemented with three different masks, with the input signal being the sound produced by the RPT device blower. Each mask in this example was tested at two different operational speeds of the blower, namely 10 krpm and 15 krpm. Although these speeds were used in the examples, the methodology may be implemented with other blower speeds particularly if the resulting sound is detectable by the microphone.

In FIG. 9, the reflection component can clearly be seen in all six cepstra, beginning at around a quefrency of twelve milliseconds (12 ms). This position is as expected (2L/c) since in the example therapy system, a two-meter conduit was used and the speed of sound is 343 m/s. In FIG. 9, the graph illustrates cepstra from masks in the following order from top to bottom:

ResMed Ultra Mirage™ at 10 krpm;
ResMed Ultra Mirage™, at 15 krpm;
ResMed Mirage Quattro™ using the at 10 krpm;
ResMed Mirage Quattro™ at 15 krpm;
ResMed Swift II™ at 10 krpm; and
ResMed Swift II™ at 15 krpm.

Although FIG. 7 illustrates the system 7000 having a single microphone 7050, in one or more alternative implementations, there can be multiple microphones. FIG. 14 illustrates such a system 1400, according to an aspect of the present technology. The system 1400 is identical to the system 7000 of FIG. 7, except for the following described differences. Thus, the features in FIG. 14 are identical to the features described with respect to and labelled in FIG. 7 with analogous label numbers, unless otherwise noted.

The system 7000 includes a first microphone 1450 and a second microphone 1460, both similar to the microphone 7050. The first microphone 1450 is separated from the second microphone 1460 along the air circuit. In one implementation, the separation distance is L, the length of the conduit 1410. The system 1400 includes an acoustic analysis apparatus 1415 that is in communication with the first microphone 1450 via a connection 1425 and with the second microphone 1460 via a connection 1435.

In one or more implementations, the second microphone 1460 can provide higher precision, such as the ability to provide extra ranging information (modelling time of flight from one or more sound sources), noise reduction, or other functionality. In some implementations, the first microphone 1450 senses sound within the conduit 1410 and the second microphone 1460 senses the environment outside the conduit 1410 or RPT device/humidifier 1440 (e.g., background noise). For systems with two or more microphones, the signal processing may be arranged to remove patient sounds or other interfering noises in the environment from the reflection of sound generated by the RPT device/humidifier 1440, thereby increasing the signal to noise ratio of the system 1400.

In other implementations, the second microphone 1460 is used to sense sound within the conduit 1410. Sound is generated by the RPT device/humidifier 1440 and travels down the conduit 1410. The time required for sound to travel from the RPT device/humidifier 1440 to the first microphone 1450, and then from the first microphone 1450 to the second microphone 1460, is dependent on the speed of sound c within the conduit 1410.

Generally, the delay between the time at which a generated sound appears at the first microphone 1450 and the time at which the same generated sound appears at the second microphone 1460 is about L/c, where L is the length of the conduit 1410 between the first and second microphones 1450 and 1460 and c is the speed of sound in the conduit 1410. Such implementations are referred to as "transmission-based systems" to distinguish them from reflection-based systems in which the delay is about 2L/c.

In a transmission-based system, the cepstrum $\tilde{Y}_1(\tau)$ of the signal generated by the first microphone 1450 comprises an input signal component $\tilde{S}_1(\tau)$ concentrated around quefrency zero. The cepstrum of the signal $\tilde{Y}_2(\tau)$ generated by the second microphone 1460 comprises an IRF cepstrum $\widetilde{H_l}(\tau)$ (the acoustic signature of the transmission-based system), which is approximately a single peak at a quefrency of L/c, added to the input signal component $\tilde{S}_1(\tau)$. The acoustic signature $\widetilde{H_l}(\tau)$ may therefore be obtained by subtracting the cepstrum $\tilde{S}_1(\tau)$ from the cepstrum $\tilde{Y}_2(\tau)$. The delay of the acoustic signature may then be estimated as the quefrency location of the peak of the acoustic signature $\widetilde{H_l}(\tau)$. The acoustic signature in a transmission-based system such as the system 1400 does not represent a characteristic of the mask 1420, only a characteristic of the conduit 1410, and therefore is unsuitable for mask identification or other mask characteristic analysis.

5.8.1.1 Back Reflection Minimisation

One complicating factor in acoustic signature extraction is acoustic "back-reflections" from the device (RPT device) end of the conduit 7010. These back-reflections occur from the device end of the conduit 7010 after the sound reflected from the mask 7020 has travelled back along the conduit 7010, as a result of the change in acoustic impedance between the conduit 7010 and the interior cavity of the RPT device/humidifier 7040 to which the conduit 7010 is connected. Such back-reflections have a muddying effect on the acoustic signature of the mask. For some implementations, acoustic signature analysis would therefore be made more accurate if back-reflection could be reduced or minimised. For example, when the dimensions of the mask are of a similar physical scale to the distance between the acoustic sensor and any discontinuity in the cross-sectional area inside the flow generator, the reflection from the mask may be superimposed in the output signal on the response of the flow generator back-reflection. In some cases, it may be desirable to characterize the back-reflections and deconvolve them from the component reflection. It may however be desirable to minimise the back reflections by design.

In one such implementation, illustrated in FIG. 10, the end of the conduit 1010 nearest the microphone 1050 comprises structure 1060 configured to reduce back-reflection. The structure 1060 is illustrated as a horn that extends from the device end of the conduit 1010, where its diameter is the same of that of the conduit 1010, into an interior cavity of the RPT device/humidifier 1040 with a gradually increasing diameter. Because acoustic impedance of an acoustic waveguide is related to the diameter of the waveguide, the horn structure 1060 minimises back-reflection by gradualising the change in acoustic impedance between the conduit 1010 and the cavity of the RPT device/humidifier 1040. The horn structure 1060 may be of conical profile as illustrated in FIG. 10, or the cross-section of the horn may curve in the manner of the bell of a brass instrument. The effect of the horn structure 1060 is to reduce the back-reflection component in the acoustic signature of a system component 1020.

5.8.1.2 Spectral Flattening

Subtracting a low-pass filtered version of the log spectrum $\mathrm{Log}\{Y(f)\}$ from itself, e.g. subtracting a moving average of the log spectrum $\mathrm{Log}\{Y(f)\}$ from the log spectrum $\mathrm{Log}\{Y(f)\}$, before performing the IFT in Equation (5) to compute the cepstrum $\tilde{Y}(\tau)$, may flatten the global shape of the log spectrum and reduce the sensitivity of the separation of the acoustic signature to the randomness of the input signal $s_1(t)$. That is, such flattening will concentrate the input signal component $\tilde{S}_1(\tau)$ in the output cepstrum $\tilde{Y}(\tau)$ around the origin ($\tau=0$) even if the input signal $s_1(t)$ is not particularly random in character. This concentration increases the separability of the input signal component $\tilde{S}_1(\tau)$ from the reflection component of the system IRF (the acoustic signature) in the output cepstrum $\tilde{Y}(\tau)$. Care needs to be taken to set the filter such that the conduit resonant frequency is not removed in the flattening process. For example, the filter cut-off point should be low enough (or the window of the moving average long enough) that the conduit resonance is significantly removed by the filter, and thus preserved by the flattening process. In an alternative implementation, the log spectrum $\mathrm{Log}\{Y(f)\}$ may be high-pass filtered before performing the IFT in Equation (5) to compute the cepstrum $\tilde{Y}(\tau)$.

5.8.2 Acoustic Signature Delay Analysis

The output cepstrum $\tilde{Y}(\tau)$ may be computed over a finite time window of the sampled output signal y(t). A longer window may produce a cleaner separation between the acoustic signature and the input signal component. However, since the acoustic characteristics of the airpath may vary over time due to such factors as the change in gas composition over the breathing cycle, changes in humidity, and tube drag (which may lengthen the airpath unpredictably), the window should not be made so long that significant variation of the airpath characteristics over the window may be expected. In one example, the window is of duration about 200 ms. Other suitable window durations may be implemented.

Multiple output cepstra $\tilde{Y}(\tau)$ may be computed over multiple windows, and the delay of the acoustic signature extracted from each window may be estimated. The result is a time series of acoustic signature delay estimates. Such a time series of delay estimates may be implemented using any suitable data structure for analysis or processing, such as an array, vector, buffer, etc. As mentioned above, in a reflection-based system the delay of the acoustic signature is equal to 2L/c (wherein L is the length of the conduit, and c is the speed of sound in the conduit), while in a transmission-based system the delay of the acoustic signature is equal to L/c. Variations in the acoustic signature delay therefore reflect variations in the length of the conduit and/or the speed of sound in the conduit.

The speed of sound in a gas mixture varies with the composition of the mixture. In particular, the speed of sound c in the conduit of a respiratory therapy system decreases as the concentration of carbon dioxide in the conduit rises.

For example, if a two-meter conduit appears two meters long (based on the speed of sound in atmospheric air at room temperate and pressure), once the conduit is filled up with a higher concentration of carbon dioxide, the effective length of the conduit appears to change. This is because the speed of sound in carbon dioxide gas is about 267 meters per second (m/s) at 20° C., and the speed of sound in atmospheric air is around 343 m/s at 20° C. Accordingly, analyzing sounds within the conduit through cepstrum analysis, or other signal processing techniques, can take advantage of this property of sound to estimate the concentration of carbon dioxide in the conduit.

In general, the concentration of carbon dioxide in the conduit of a respiratory therapy system varies over the breathing cycle, being greatest at the end of expiration and lowest at the end of inspiration. According to one estimate, at 20° C., the speed of sound in a respiratory conduit varies by about 0.67% over the breathing cycle due to this change in the concentration of $CO_2$. This variation will be reflected as a cyclical variation in the delay of the acoustic signature at the breathing rate. It is safe to assume that the length L of the conduit does not vary cyclically with the breathing cycle. Consequently, analysis of a time series of acoustic signature delay estimates, and in particular variation in the delay estimates, such as in relation to a component thereof from a frequency band around the patient's breathing rate, will yield information about the concentration of $CO_2$ in the conduit of the respiratory therapy system. Optionally, determining the concentration of $CO_2$ can involve correcting for one or more environmental parameters, such as temperature, humidity, pressure, ambient $CO_2$ concentration, background noise, and so forth (e.g., based on device settings, humidifier in use or not and configuration thereof, and type of conduit, whether heated or not, etc.).

FIG. 11 is a flow chart illustrating a method 11000 of estimating acoustic signature delay of the airpath of a respiratory therapy system in accordance with one aspect of the present technology. The method 11000 may start at step 1110, which computes the output cepstrum $\tilde{Y}(\tau)$ from the output signal y(t) during a window as described above in relation to equation (5). Step 1110 optionally flattens the log spectrum Log{Y(f)} before computing the output cepstrum $\tilde{Y}(\tau)$ as described above.

Step 1120 follows, at which the reflection component (acoustic signature) is separated from the cepstrum computed at step 1110. At the next step 1130, the delay of the acoustic signature is estimated and recorded along with the time of the corresponding window.

Step 1140 then checks whether more acoustic signature delays are to be obtained. If so ("Y"), the method 11000 proceeds to step 1160, which awaits the next window before returning to step 1110 to compute a new cepstrum from the next window. If not ("N"), the method 11000 concludes at step 1150.

5.8.2.1 Breathing-Rate Frequency Band Analysis (e.g. $CO_2$ Concentration and/or Cardiac Output)

The time series of acoustic signature delay estimates may be band-pass filtered to the breathing rate frequency band to extract an acoustic signature delay time series whose variation is largely due to the variation in $CO_2$ concentration in the conduit. The breathing rate frequency band for a normal adult at rest is approximately 0.1 Hz to 0.5 Hz.

The band-pass filtered delay time series may be converted to a time series of speed of sound estimates c by dividing the current length L of the air circuit by each delay estimate, such as for a transmission-based system. In a reflection-based system such as the system 7000, the resulting estimate may then be multiplied by two. The speed of sound estimates c may in turn be converted to estimates of $CO_2$ concentration in the air circuit using the properties of nitrogen, oxygen, and $CO_2$.

In one implementation, a simple model of the speed of sound c in a gas mixture as the weighted sum of the speeds of sound $c_i$ in the gases of the mixture weighted by their fractional concentrations $p_i$ may be used:

$$c = \sum_i p_i c_i \tag{6}$$

Table 1 contains estimates of the speed of sound $c_i$ in the pure forms of the four main constituent gases in atmospheric air at room temperature, along with their typical fractional concentrations $p_i$ in atmospheric air.

TABLE 1

Properties of gases in atmospheric air

| i | Pure Gas | Speed of sound $c_i$ (metres per second) | Fractional concentration in atmospheric air ($p_i$) |
|---|---|---|---|
| 1 | Nitrogen | 349 | .78 |
| 2 | Argon | 319 | .0097 |
| 3 | Oxygen | 326 | .21 |
| 4 | Carbon dioxide | 267 | .0003 |

Assuming that the fractional concentrations $p_1$ and $p_2$ of nitrogen and argon in the air circuit do not change over the breathing cycle, the concentrations of oxygen and carbon dioxide in the air circuit change over the breathing cycle in complementary fashion. This means that if the fractional concentration of carbon dioxide at any instant of time is written as p, the fractional concentration of oxygen may be written as $(1-(p_1+p_2)-p)$. Substituting these values into Equation (6), an expression for the fractional concentration p of $CO_2$ in terms of the measured speed of sound c in the air circuit may be derived:

$$p = \frac{p_1 c_1 + p_2 c_2 + (1 - (p_1 + p_2))c_3 - c}{c_3 - c_4} \quad (7)$$

Using the values from Table 1, Equation (7) may be simplified to the following formula relating the measured speed of sound c to the fractional concentration p of $CO_2$ in the air circuit:

$$p = \frac{343.87 - c}{59} \quad (8)$$

Thus, a system may be configured to generate one or more $CO_2$ concentration indications, or variations therein, based on the filtered time series of acoustic signature delay estimates, where the filtering serves to isolate or include frequencies associated with respiration frequency. Such a generation may include one or more output signals comprising a displayed or communicated message and/or a control signal that changes or alters a provided therapy (e.g., pressure or flow) based on the indications and/or an evaluation thereof, that can be taken such as if the determined concentration indication satisfies (e.g., exceeds) a threshold.

For example, FIG. 12 contains two contemporaneous time series plotted on the same time axis. The upper trace 1200 is a time series of estimated acoustic signature delay values band-pass filtered to the breathing rate frequency band. The lower trace 1250 is a time series of contemporaneous $CO_2$ concentration measurements from a $CO_2$ sensor in the plenum chamber of a mask for which the acoustic signatures giving rise to the trace 1200 were reflected. It may be seen that peaks, e.g. 1210, in the acoustic signature delay trace 1200, i.e. instants of increased delay or slowest speed of sound, coincide with peaks, e.g. 1260, in the measured $CO_2$ concentration due to exhalation, as expected, since the speed of sound in air decreases as the concentration of $CO_2$ in the air increases.

By way of additional example, from the indication of variation of $CO_2$ concentration in the conduit over the respiratory cycle, other actionable information may also be extracted. In one example, the fractional concentration of $CO_2$ in the conduit at the end of expiration (end-tidal $CO_2$ concentration, or $EtCO_2$), i.e. the peak value of $CO_2$ concentration over the respiratory cycle, may be used in a modified Fick technique for measuring a patient's cardiac output. The modified Fick technique [1] involves imparting a step change to the deadspace of a respiratory therapy system and measuring the effect on $EtCO_2$ to estimate the patient's cardiac output. In one implementation of the modified Fick technique, the effective volume of the deadspace may be altered by a change to a CPAP treatment pressure or a HFT flow rate. For example, a lower pressure or flow rate increases the effective deadspace by lowering the washout flow rate through the system vents. The resulting change in $EtCO_2$ may be estimated and converted to an estimate of the patient's cardiac output.

FIG. 15 is a flow chart illustrating an example of a process 1500 for determining the cardiac output of a patient, according to an aspect of the present technology. While the process 1500 is described below as being executed by an acoustic analysis apparatus such as the acoustic analysis apparatus 7015, the process 1500 may also be executed by the central controller 4230 as part of the algorithms 4300 as described above.

At step 1510, the acoustic analysis apparatus determines a measure of sound using at least one sound sensor within a conduit coupled to a patient. The sound sensor can be the microphone 7050 detecting various sounds within a conduit, such as a conduit 7010 of the respiratory therapy system 7000. In one or more embodiments, prior to or at the same time as step 1510, a sound can be generated within the conduit by a sound source. The sound source can be an element of a respiratory therapy system, such as the RPT device/humidifier 7040, where the conduit is part of an airpath of the respiratory therapy system, such as a continuous positive air pressure ("CPAP") system or similar system. Alternatively, the sound source can be a speaker, both where the conduit is part of an airpath of a respiratory therapy system and where the conduit is separate from an airpath of a respiratory therapy system. The measure of sound may be a measure of sound within the conduit generated by the sound source. In one or more embodiments, the at least one sound sensor may be a microphone, and the conduit can be part of an airpath of a respiratory therapy system to which the microphone is coupled.

At step 1520, the acoustic analysis apparatus determines a carbon dioxide concentration within the conduit based, at least in part, on the measure of sound. In one or more embodiments, determining the carbon dioxide concentration can include calculating a Fourier transform of data samples representing the measure of sound. In one or more embodiments, determining the carbon dioxide concentration can further include calculating a logarithm of the Fourier transform of the data samples representing the measure of sound. In one or more embodiments, determining the carbon dioxide concentration can further include calculating an inverse Fourier transform of the logarithm of the Fourier transform of the data samples representing the measure of sound. In one or more embodiments, determining the carbon dioxide concentration further includes calculating a difference between (a) the inverse Fourier transform of the logarithm of the Fourier transform of the data samples representing the measure of sound and (b) an inverse Fourier transform of a logarithm of a Fourier transform of data samples representing a baseline carbon dioxide concentration in the airpath of the respiratory therapy system.

In one or more embodiments, the acoustic analysis apparatus can determine one or more environmental parameters of the conduit or the respiratory therapy system, such as with sensors configured to detect such parameters and/or other data input to the system. The one or more environmental parameters can include any one or more of air temperature, ambient pressure, ambient carbon dioxide concentration, background noise, or a combination thereof. Subsequently, the acoustic analysis apparatus can correct for the one or more environmental parameters when determining the carbon dioxide concentration. For example, the temperature can affect the speed of sound within the conduit. Accounting for the temperature accounts for the effects of temperature on the speed of sound such that the subsequent determination of the carbon dioxide concentration is more accurate.

With respect to the ambient carbon dioxide concentration, in one or more embodiments, the acoustic analysis apparatus can determine the baseline carbon dioxide concentration in the conduit while the conduit is not coupled to the patient. In these circumstances, the concentration of the carbon dioxide within the conduit is representative to the ambient concentration of carbon dioxide. Alternatively, or in addition, the acoustic analysis apparatus can query one or more external databases that have information on the carbon dioxide concentration for the location of the acoustic analysis apparatus. Alternatively, or in addition, the acoustic analysis apparatus can include a carbon dioxide sensor that can directly sense the concentration of carbon dioxide in the conduit, rather than indirectly by determining the measure of sound. The acoustic analysis apparatus can compare the determined carbon dioxide concentration through determining the measure of sound with the carbon dioxide concentration from the carbon dioxide sensor to validate the carbon dioxide concentration.

In one or more embodiments, the sound sensor can detect the background noise. For example, the sound sensor can detect the background noise before the patient is coupled to the conduit. For example, in the case of the conduit being part of an airpath of a respiratory therapy system, the at least one sound sensor can detect the background noise before the patient begins using the respiratory therapy system. Alternatively, where the measure of sound is based on a sound source within the conduit, the at least one sound sensor can detect the background noise prior to, or after, the sound source generates the sound, or both prior to and after the sound source generates the sound.

At step 1530, the acoustic analysis apparatus determines the cardiac output of the patient based, at least in part, on the carbon dioxide concentration. Determining the cardiac output of the patient can be based, at least in part, on the modified Fick method discussed above, and based, at least in part, on the carbon dioxide concentration. The modified Fick method relies on Equation (9):

$$CO = \frac{VCO_2}{CvCO_2 - CaCO_2} \tag{9}$$

where CO is the cardiac output; $VCO_2$ is the exhaled carbon dioxide concentration; $CvCO_2$ is the venous carbon dioxide content; and $CaCO_2$ is the arterial carbon dioxide content.

Assuming that the cardiac output remains unchanged under normal (N) and rebreathing (R) conditions, Equation (9) results in:

$$CO = \frac{VCO_{2N}}{CvCO_{2N} - CaCO_{2N}} = \frac{VCO_{2R}}{CvCO_{2R} - CaCO_{2R}} \tag{10}$$

By subtracting the normal and rebreathing ratios, the following differential Fick Equation is obtained:

$$CO = \frac{VCO_{2N} - VCO_{2R}}{(CvCO_{2N} - CaCO_{2N}) - (CvCO_{2R} - CaCO_{2R})} \tag{11}$$

Because carbon dioxide diffuses quickly in blood (i.e., 22 times faster than oxygen), one can assume that $CvCO_2$ does not differ between normal and rebreathing conditions, and therefore the venous contents disappear from the numerator of Equation (11), leaving Equation (12):

$$CO = \frac{\Delta VCO_2}{\Delta CaCO_2} \tag{12}$$

The delta in $CaCO_2$ can be approximated by the delta in etCO2 multiplied by the slope (S) of the carbon dioxide dissociation curve. This curve represents the relation between carbon dioxide volumes (used to calculate carbon dioxide content) and partial pressure of carbon dioxide. This relation can be considered linear between 15 and 70 mmHg of partial pressure of carbon dioxide, resulting in Equation (13):

$$CO = \frac{\Delta VCO_2}{S \times \Delta etCO_2} \tag{13}$$

According to the foregoing, the cardiac output of a patient can be determined based on the carbon dioxide concentration of the exhaled breath of the patient. Thus, a patient can use a respiratory therapy system throughout a sleep session, such as throughout the night while the patient is sleeping. During use, the acoustic analysis apparatus of the present technology within or separate from the respiratory therapy system can determine the cardiac output of the patient. Such a determination can be done non-invasively and without disturbing the patient. Yet, the patient or other user can gain the additional understanding of the patient's cardiac output.

The process 1500 of FIG. 15 can be done once to determine a discrete cardiac output of the patient. Alternatively, one or more of the process steps of the process 600 can be repeated. For example, determining the carbon dioxide concentration and determining the cardiac output both can be done for a plurality of times during a single session to determine multiple discrete cardiac outputs of the patient. As mentioned above, where the conduit is part of a respiratory therapy system, the session can be during use of the respiratory therapy system during a single night or over the course of multiple different nights. The acoustic analysis apparatus can subsequently determine a trend in the cardiac output for the session. Based on the trend, one or more actions can be taken. For example, the trend may indicate a worsening in the cardiac output. In which case, the patient may be notified so that medical treatment can be sought. Alternatively, the trend may indicate an improving in the cardiac output. In which case, medical treatment can be stopped or lessened.

The cardiac output of a single session or multiple sessions can be compared to population normative values of age, gender, cardiac health, medication regime and so forth as one or more thresholds. Action, such as generation of one or more output signals comprising a displayed or communication message and/or a control signal that changes or alters a set point of a therapy device that produces a therapy (e.g., pressure or flow) based on the cardiac output and/or an evaluation thereof, may be taken conditioned on the comparison, such as if the determined cardiac output satisfies (e.g., exceeds) a threshold. Trend data can be used to detect the typical baseline of a patient to (a) aid the acoustic analysis apparatus in identifying cardiac output that is not accurate based on one or more issues with the acoustic analysis apparatus, and (b) detect changes in the patient's data that are indicative of a worsening (or improving) trend in their cardiac output. Where a worsening trend is observed, the system may generate the output to recommend a check-up by a healthcare professional. For example, heart failure via edema can be seen via a reduction in cardiac output. Detection of a reduction in cardiac output can be representative of heart failure. Detection of a reduction in cardiac output by the present acoustic analysis apparatus allows the patient to seek medical attention in response to generated output message based on the analysis. Chronic Obstructive Pulmonary Disease (COPD) exacerbations may also be predicted or detected using such an approach.

In one or more embodiments, signals from the pressure sensor, flow sensor, speed sensor, or other sensors within a respiratory therapy system can be analyzed for rate and depth of breathing (increased rate and shallower breaths). This information may be used in conjunction with heart rate and/or cardiac output in order to predict or detect a cardiac decompensation. Other parameters of the patient using the respiratory therapy system can be combined with the cardiac output. Such parameters can include tidal volume, minute ventilation, etc.

Although an integrated acoustic analysis apparatus and respiratory therapy system with cardiac output detection are contemplated by the present technology, the methodology of the components of the apparatuses may be shared across multiple components within a system. For example, a measuring device may simply conduct the measuring processes to determine the delay of a conduit and transfer the data to another processing system. The second processing system may in turn analyze the data to determine the carbon dioxide concentration, which can in turn send the data to another device for determining the cardiac output, as previously discussed. The third processing system may then indicate the cardiac output as described herein, such as by sending one or more of the described messages, in electronic form, for example, back to the measuring device or other apparatus for display to the patient or a clinician or physician.

Other examples of the use of $EtCO_2$ are:

- Monitoring the progression of COPD.
- Titrating ventilation parameters such as pressure support, volume delivery, and minute ventilation target.
- Determining the correct placement of an endo-tracheal tube in the trachea.

5.8.2.2 Additional Breathing-Rate Frequency Band Analysis (e.g., $CO_2$ Distribution)

As with the delay of the acoustic signature as a whole, analysis of a time series of acoustic signature internal delay estimates, in particular a component thereof from a frequency band around, and including, the patient's breathing rate, will yield information about the concentration of $CO_2$ in the mask tube. More generally, analysis of breathing-rate-frequency-band variations in the structure of the acoustic signature of a mask of any type, which comprises a discrete series of reflection components corresponding to different structures along the airpath of the mask, may yield information about the distribution of the relative concentration of $CO_2$ in various parts of the mask. Combining this with analysis of the acoustic signature delay, which indicates the concentration of $CO_2$ within the conduit 7010, a picture of the distribution of $CO_2$ within the pneumatic circuit, and its evolution over time, may be built up. From this picture, actionable information may be extracted. In one example, an increase in the relative concentration of $CO_2$ towards the RPT device/humidifier 7040 may be an indication that washout of exhaled $CO_2$ by the system venting is inadequate, and consequently $CO_2$ rebreathing is excessive, which can lead to central apneas, headaches, or a feeling of stuffiness. Thus, the system may be configured to generate one or more output signals comprising a displayed or communicated message and/or a control signal that changes or alters a provided therapy (e.g., pressure or flow or controlled adjustment of a vent area such as a mask vent) based on the distribution of $CO_2$ or changes in the distribution.

5.8.2.3 Non-Breathing-Rate Frequency Band Analysis (e.g. Conduit Length)

The variations in the acoustic signature delay time series that are not within the breathing rate frequency band are not respiratory-related. Removing the breathing-rate-frequency-band variations from the original delay time series, such as by subtracting the band-pass filtered version of the delay time series from the original delay time series, therefore gives a time series of non-respiratory-related delay estimates. The principal source of non-respiratory-related delay variations is variation in conduit length L. Each delay value in a non-respiratory-related time series may be mapped to a value of conduit length L by multiplying the delay value by c/2 (for a reflection-based system) or c (for a transmission-based system), where c is the speed of sound in atmospheric air (approximately 343 m/s at 20° C.).

The variations in the conduit length L as detected with the non-respiratory-related acoustic delay time series, may be taken as an indication of the status of the patient or the respiratory therapy system. For example, as mentioned above, tube drag is one possible cause of change in conduit length. Tube drag varies as the patient's sleeping position changes over the therapy session. Therefore, variability in conduit length over a therapy session may be taken as an indication of the patient's activity or restlessness during the therapy session. Such patient activity may be used or implemented in a system in a number of ways:

- As an indicator of therapy effectiveness.
- As an indicator of sleep state (asleep/awake).
- As an adjunct to processes that detect apneas or hypopneas. Apneas or hypopneas that coincide with periods of high activity may be disregarded or discounted by therapy algorithms as they are less likely to represent true airway obstructions.

Also, a cumulative measure of tube drag may be used as an indicator of conduit life, since persistent drag causes the conduit 7010 to lose its elasticity. In one example, a long-term increase in the conduit length can be taken as an indication that the conduit 7010 is permanently stretched. The respiratory therapy system may therefore, by analysing the statistics of conduit length variation over many therapy sessions, determine or predict when an increase in the conduit length over many therapy sessions is or will be greater than a threshold, and thus estimate or predict when a conduit is or will be due for replacement. Based on such an assessment, the system may trigger generation of one or more output messages to indicate or offer replacement.

5.8.3 Acoustic Signature Shape Analysis (e.g., Mask Tube or Headgear)

In further embodiments of the present technology, the shapes of acoustic signatures in reflection-based systems may be analyzed by the system to detect particular characteristics of masks. For example, acoustic signatures may be analyzed by the system to detect characteristics of masks. The characteristics may include: diameter, construction materials, volume of air cavities, overall configurations of the mask, etc.

One such characteristic of a mask is the length of the mask tube, which may be detected from the shape analysis of the acoustic signature. The acoustic signature of a mask with a mask tube comprises two separate portions, a portion corresponding to reflection of sound from the connection port 3600 between the air circuit 4170 and the mask tube, and a portion, delayed in quefrency from the first portion, corresponding to reflection of sound from the body of the mask 3000. The delay between the two portions is equal to twice the length of the mask tube divided by the speed of sound in the mask tube.

FIG. 13 is a graph containing a cepstrum 1300 of a pillows mask 7020 including a mask tube in the respiratory therapy system 7000. The portion of the cepstrum 1300 corresponding to the acoustic signature is indicated as 1350. The portion 1310 of the acoustic signature 1350 corresponds to reflection of sound from the connection port 3600 between the air circuit 4170 and the mask tube. The portion 1320 of the acoustic signature corresponds to reflection of sound from the body of the pillows mask. The "internal delay" 1330 between the two portions 1310 and 1320 is equal to twice the length l of the mask tube divided by c (the speed of sound in the mask tube).

Another characteristic of a mask is headgear elasticity. When headgear is used as the positioning and stabilising structure 3300, the headgear stretches. The effect of the stretching is that the seal-forming structure 3100 is less compressed against the patient's face. This reduction in compression may show up as a change in the portion of the acoustic signature corresponding to reflection of sound from the body of the mask. The respiratory therapy system may therefore, by analysing the portion over many therapy sessions, be able to estimate or predict when a mask or will be is due for replacement because of headgear stretching. For example, the detection of a displacement or other change in shape of the portion, such as from a prior shape or location of the portion, may serve as a basis for a replacement indication. Thus, based on such an assessment, the system may trigger generation of one or more output messages to indicate or offer replacement.

5.8.3.1 Non-Breathing-Rate Frequency Band Analysis (e.g., Mask Tube Length)

As with the delay of the acoustic signature as a whole, non-respiratory-related variations in the internal delay of the mask signature may be obtained by removing the breathing-rate-frequency-band variation from the original internal delay time series, such as by subtracting the band-pass filtered version of the internal delay time series from the original internal delay time series. The resulting non-respiratory-related variations in the internal delay time series may be multiplied by c/2 to obtain a time series of variations in the mask tube length l. Thus, in addition to or alternatively to shape analysis as previously described, mask tube length variation may be derived with filtering.

Tube drag causes variation in the mask tube length l as well as in the length L of the air circuit. In one implementation, a long-term increase in the mask tube length indicates that the mask tube is permanently stretched. The respiratory therapy system may therefore, by analysing the statistics of mask tube length variations over many therapy sessions, be able to assess the current life of the mask. In particular, by analysing the statistics to determine or predict when an increase in the mask tube length over many therapy sessions is or will be greater than a threshold, the respiratory therapy system may be able to estimate or predict when a mask is or will be due for replacement because of mask tube stretching.

In another implementation, variability in mask tube length over a therapy session may be used as a proxy for or indication of the patient's activity or restlessness during the therapy session.

5.8.4 Example System Design Implementations

The signal processing analysis described in relation to FIGS. 11 and 15, as well as the additional methodologies described herein using the aforementioned delay detections and cepstrum or quefrency related analysis etc., may be implemented by a controller or processor, such as with firmware, hardware and/or software as previously discussed. In some example implementations, such a controller may estimate $CO_2$ concentration at one or more locations within the respiratory therapy system. This $CO_2$ concentration data, and/or cardiac output data from the modified Fick technique, may then be relayed to a further controller, processor, system or computer or used by the controller. The information then may be utilized in adjusting therapy or other settings for the control of the RPT device in the delivery of respiratory therapy by the respiratory therapy system.

For example, the aforementioned technology may be implemented as part of a controller of a respiratory therapy system such as CPAP apparatus.

Alternatively, the aforementioned technology may be implemented by an acoustic analysis apparatus such as the acoustic analysis apparatus 7015 of FIG. 7 that may be external to a CPAP apparatus such that the acoustic analysis apparatus itself does not include a pressure generator (e.g., flow generator). For example, such a monitoring apparatus may be implemented as illustrated in FIG. 16. In this regard, FIG. 16 is a diagram of the components of an implementation of the acoustic analysis apparatus 7015 of FIG. 7, according to one aspect of the present technology. By way of example, the acoustic analysis apparatus 1600 in FIG. 16 includes one or more components for determining the cardiac output of a user, in addition to performing the other functions described above. It is contemplated that the functions of these components may be combined in one or more components or performed by other components of equivalent functionality.

One or more processors, such as the processor 1602, performs a set of operations on information, such as the data samples representing the measure of sound from a sound transducer, as specified by computer program code. The code may further process such data to produce $CO_2$ concentration indications, and/or other output as previously described such as that related to detecting the cardiac output of the user, in addition to any one or more methodologies discussed herein. The computer program code is a set of instructions or statements providing control instructions for the operation of the processor 1602 to perform specified functions. The code, for example, may be written in a computer programming language that is compiled into a native instruction set of the processor 1602. The code may also be written directly using the native instruction set (e.g., machine language). The set of operations typically include comparing two or more units of information, shifting positions of units of information, and combining two or more units of information, such as by addition or multiplication or logical operations like OR, exclusive OR (XOR), and. Each operation of the set of operations that can be performed by the processor 1602 is represented to the processor 1602 by information called instructions, such as an operation code of one or more digits. A sequence of operations to be executed by the processor 1602, such as a sequence of operation codes, constitute processor instructions, also called computer system instructions or, simply, computer instructions.

The memory 1604 stores information, including processor control instructions as previously described, such as for determining the cardiac output of the user, along with the other methodologies disclosed herein. It may further store data produced or received data, such as sound signal data and output data, such as cepstrum data, acoustic signature data, delay data, delay time series data (filtered and/or unfiltered), $CO_2$ concentration data, cardiac output data etc. The memory 1604 can be random access memory (RAM) or any other dynamic storage device. Dynamic memory allows information stored therein to be changed by the processor 1602. RAM allows a unit of information stored at a location (e.g., memory address) to be stored and retrieved independently of information at neighboring addresses. The memory 1604 is also used by the processor 1602 to store temporary values during execution of instructions. Alternatively, or in addition, the memory 1604 can be read only memory (ROM) or any other static storage device coupled for storing static information, including instructions, that are not changed.

In one or more embodiments, the memory 1604 can include stored processor control instructions for sound signal processing and acoustic analysis, such as measurement filtering, Fourier transforms, logarithm, position determination, extent determination, difference determination, etc. In one or more embodiments, the processor control instructions and data for controlling the disclosed methodologies can be contained in the memory 1604 as software for use by the processor 1602 to be specific purpose processors according to any of the methodologies discussed herein.

In one or more embodiments, the acoustic analysis apparatus 1600 can optionally include a display 1606, such as a monitor, an LCD panel, a touch screen, etc. for presenting output data. The acoustic analysis apparatus 1600 can also optionally include a control interface 1608, such as a keyboard, a touch panel, control buttons, a mouse, etc. for inputting data or otherwise activating or operating the methodologies described herein. The acoustic analysis apparatus 1600 can also optionally include a data interface 1610, such as a bus, for receiving/transmitting data, such as programming instructions, settings data, sound data, etc. to another device, such as the sound sensor 104.

Additionally, in some embodiments, the information obtained from delay analysis may be selectively transmitted to other systems, such as to one or more servers, for communicating such information to a manufacturer, doctor or clinician, etc., so that the information may be used to assist patients with troubleshooting. For example, such data could be transmitted by wired and/or wireless communications such as wireless communication protocols, including, for example, Bluetooth™ and/or WiFi™ or other communications protocol(s).

Additionally, in some embodiments, the information obtained from delay analysis may be used to trigger action such as manual or automated deployment of personalised coaching or training content related to the particular mask, for example, a tutorial on making adjustments to the mask. Such material may be communicated to a user via the therapy device screen or a supporting mobile device application, or other means of communication such as email or SMS message. In one example, excessively high or low $CO_2$ concentration may trigger a recommendation to increase or decrease the treatment pressure or flow rate, or to change the mask type.

In some embodiments, greater blower speeds than the speeds illustrated above may be implemented during acoustic signature delay estimation. For example, some conduits use materials with properties that may reduce noise. In such a system, the acoustic losses of the system may fluctuate. If the losses increase as detected by the measured signal (e.g., amplitude decrease), the decibels of the sound or noise source may be increased to overcome the effects of sound loss. This may be achieved by increasing the speed of the blower during a test measurement process. Additionally, other elements included in the airpath may increase the acoustic losses. These elements may include: humidifiers, noise baffles, and valves. Again, the loss attributable to these components may also be overcome by increasing the noise source level or amplitude. Typically, a suitable sound level for the input signal may be about 20 dBa or greater.

The frequency range of the microphone 4270 may be selected according to the geometric resolution required for the delay estimation. Resolving information about small dimensions will typically require high frequency content in the generated sound signal. A typical air circuit for respiratory therapy might exhibit tube resonances with a fundamental frequency of less than 100 Hz, but with higher harmonics appearing in the spectrum as integer multiples of the fundamental frequency up to more than 10 kHz. The frequency range of the microphone 4270 may be selected to be large enough to allow sensing of enough of the resonant harmonics that the periods associated with the harmonic spacing are present in the inverse Fourier Transform of the log spectrum. In one implementation, therefore, the microphone 4270 may be configured to detect frequencies up to an upper frequency limit of at least 10 kHz.

As previously mentioned, some embodiments may utilize a sound source such as a speaker to generate a sound impulse or white noise. This may be particularly useful for respiratory therapy systems with very quiet blowers that do not generate much noise. For example, when using a ResMed™ RPT device at speeds generally less than 6 krpm, the blower is very quiet. Under this condition, using only the sound of the blower as a sound source to produce the input signal might be insufficient for acoustic signature delay estimation. This may be overcome by including an additional sound source in the airpath. This may be activated during time periods of measurement such as when the mask is initially attached to the conduit. While an additional sound source might be a speaker, other sound emitters might be utilized. For example, a simple acoustic generator might be configured to vibrate in response to the flow of air from the RPT device such as a reed that may be selectively activated and deactivated (e.g., mechanically applied and removed from the airpath of the system). This may then serve to selectively create the sound impulse. Alternatively, an actuated valve of the RPT device may serve as the additional sound source.

Additionally, a sound source such as a speaker may be used to fill in gaps in the sound spectrum created by the blower. For example, a speaker may be used to produce a signal designed to have a particular spectrum such that the addition of the blower noise and the speaker sound produce a white spectrum. This may improve detection accuracy of the system as well as improve the perceived quality of the sound that the therapy device user experiences.

In some embodiments, autocorrelation (i.e., the inverse Fourier Transform of the power spectrum) may be implemented rather than cepstrum analysis.

5.9 ASPECTS OF THE PRESENT TECHNOLOGY

The following descriptive paragraphs explain additional examples of the aforementioned technology:

Example 1. A method for determining cardiac output comprising:

determining a measure of sound by at least one sound sensor within a conduit of a respiratory treatment apparatus coupled to a user;

determining a carbon dioxide concentration within the conduit based, at least in part, on the measure of sound; and determining the cardiac output of the user based, at least in part, on the carbon dioxide concentration.

Example 2. The method of example 1, wherein the conduit is an airway of a respiratory treatment apparatus.

Example 3. The method of example 1, wherein the determining the carbon dioxide concentration comprises calculating a Fourier transform from data samples representing the measure of sound.

Example 4. The method of example 3, wherein the determining the carbon dioxide concentration further comprises calculating a logarithm of the Fourier transform from the data samples representing the measure of sound.

Example 5. The method of example 4, wherein the determining the carbon dioxide concentration further comprises calculating an inverse transform of the logarithm of the Fourier transform from the data samples representing the measure of sound.

Example 6. The method of example 5, wherein the determining the carbon dioxide concentration further comprises calculating a difference between (a) the inverse transform of the logarithm of the Fourier transform from the data samples representing the measure of sound and (b) an inverse transform of a logarithm of a Fourier transform from data samples representing a baseline carbon dioxide concentration in the conduit.

Example 7. The method of example 1, further comprising:

generating a sound with a sound source within the conduit, wherein the determining the measure of sound is based on the at least one sound sensor detecting the sound from the sound source.

Example 8. The method of example 7, wherein the sound source is a flow generator within the respiratory treatment apparatus.

Example 9. The method of example 7, wherein the sound source is a speaker within the conduit.

Example 10. The method of example 1, wherein the at least one sound sensor is a microphone, and the conduit is an airway of the respiratory treatment apparatus to which the microphone is coupled.

Example 11. The method of example 1, further comprising:

determining one or more environmental parameters of the respiratory treatment apparatus; and accounting for the one or more environmental parameters during the determining the carbon dioxide concentration.

Example 12. The method of example 11, wherein the one or more environmental parameters comprise air temperature, ambient pressure, ambient carbon dioxide concentration, background noise, or a combination thereof.

Example 13. The method of example 12, wherein the background noise is detected by the at least one sound sensor.

Example 14. The method of example 12, wherein the background noise is detected by a second sound sensor, different from the at least one sound sensor determining the measure of sound.

Example 15. The method of example 1, wherein the at least one sound sensor comprises a first sound sensor and a second sound sensor, the first sound sensor being located within a different location of the conduit than the second sound sensor.

Example 16. The method of example 15, wherein the measure of sound includes a time of flight between the first sound sensor and the sound second sensor.

Example 17. The method of example 15, further comprising increasing a signal to noise ratio of the measure of sound based, at least in part, on measures of sound of the first sound sensor and the second sound sensor.

Example 18. The method of example 1, wherein the determining the carbon dioxide concentration within the conduit is based, at least in part, on a cepstrum of data samples representing the measure of sound.

Example 19. The method of example 1, wherein the determining the cardiac output of the user is based, at least in part, on a modified Fick method based, at least in part, on the carbon dioxide concentration.

Example 20. The method of example 1, further comprising:

repeating the determining of the carbon dioxide concentration and the determining the cardiac output for a plurality of times during a single session; and validating the carbon dioxide concentration, the cardiac output, or a combination thereof for the single session based, at least in part, on the carbon dioxide concentration, the cardiac output, or a combination thereof being within a threshold range for the session.

Example 21. The method of example 1, further comprising.

repeating the determining the carbon dioxide concentration and the determining the cardiac output for a plurality of times during a session; and determining a trend in the cardiac output for the session.

Example 22. The method of example 1, further comprising:

determining a background carbon dioxide level for a location of the respiratory treatment apparatus, wherein the determining the cardiac output of the user is based, at least in part, on the background carbon dioxide level for the location.

Example 23. The method of example 22, further comprising:

determining a worsening in the cardiac output based on the trend; and determining a need for intervention based on the worsening in the cardiac output.

Example 24. The method of example 1, wherein the determining the carbon dioxide concentration within the conduit is based on analyzing standing waves and harmonics with the conduit.

Example 25. A system for determining cardiac output comprising:

a respiratory treatment apparatus having a conduit coupled to a user;

at least one sensor configured to detect a measure of sound within the conduit;

memory storing machine-readable instructions; and a control system including one or more processors configured to execute the machine-readable instructions to:

determine a carbon dioxide concentration within the conduit based, at least in part, on the measure of sound; and determine the cardiac output of the user based, at least in part, on the carbon dioxide concentration.

Example 26. The system of example 25, wherein the conduit is an airway of a respiratory treatment apparatus.

Example 27. The system of example 25, wherein the one or more processors are configured to execute the machine-readable instructions to determine the carbon dioxide concentration based on calculating a Fourier transform from data samples representing the measure of sound.

Example 28. The system of example 27, wherein the one or more processors are configured to execute the machine-readable instructions to determine the carbon dioxide concentration based on calculating a logarithm of the Fourier transform from the data samples representing the measure of sound.

Example 29. The system of example 28, wherein the one or more processors are configured to execute the machine-readable instructions to determine the carbon dioxide concentration based on calculating an inverse transform of the logarithm of the Fourier transform from the data samples representing the measure of sound.

Example 30. The system of example 29, wherein the one or more processors are configured to execute the machine-readable instructions to determine the carbon dioxide concentration based on calculating a difference between (a) the inverse transform of the logarithm of the Fourier transform from the data samples representing the measure of sound and (b) an inverse transform of a logarithm of a Fourier transform from data samples representing a baseline carbon dioxide concentration in the conduit.

Example 31. The system of example 25, further comprising:

a sound source configured to generate a sound within the conduit, wherein the one or more processors are configured to execute the machine-readable instructions to determine the measure of sound based on the at least one sound sensor detecting the sound from the sound source.

Example 32. The system of example 31, wherein the sound source is a flow generator within the respiratory treatment apparatus.

Example 33. The system of example 31, wherein the sound source is a speaker within the conduit.

Example 34. The system of example 25, wherein the at least one sound sensor is a microphone, and the conduit is an airway of the respiratory treatment apparatus to which the microphone is coupled.

Example 35. The system of example 25, wherein the one or more processors are configured to execute the machine-readable instructions to:

determine one or more environmental parameters of the respiratory treatment apparatus; and account for the one or more environmental parameters when determining the carbon dioxide concentration.

Example 36. The system of example 35, wherein the one or more environmental parameters comprise air temperature, ambient pressure, ambient carbon dioxide concentration, background noise, or a combination thereof.

Example 37. The system of example 36, wherein the background noise is detected by the at least one sound sensor.

Example 38. The system of example 36, wherein the background noise is detected by a second sound sensor, different from the at least one sound sensor configured to determine the measure of sound.

Example 39. The system of example 25, wherein the at least one sound sensor comprises a first sound sensor and a second sound sensor, the first sound sensor being located within a different location of the conduit than the second sound sensor.

Example 40. The system of example 39, wherein the measure of sound includes a time of flight between the first sound sensor and the sound second sensor.

Example 41. The system of example 39, wherein the one or more processors are configured to execute the machine-readable instructions to increase a signal to noise ratio of the measure of sound based, at least in part, on measures of sound of the first sound sensor and the second sound sensor.

Example 42. The system of example 25, wherein the one or more processors are configured to execute the machine-readable instructions to determine the carbon dioxide concentration within the conduit based, at least in part, on a cepstrum of data samples representing the measure of sound.

Example 43. The system of example 25, wherein the one or more processors are configured to execute the machine-readable instructions to determine the cardiac output of the user based, at least in part, on a modified Fick method based, at least in part, on the carbon dioxide concentration.

Example 44. The system of example 25, wherein the one or more processors are configured to execute the machine-readable instructions to:

repeat the determining of the carbon dioxide concentration and the determining the cardiac output for a plurality of times during a single session; and validate the carbon dioxide concentration, the cardiac output, or a combination thereof for the single session based, at least in part, on the carbon dioxide concentration, the cardiac output, or a combination thereof being within a threshold range for the session.

Example 45. The system of example 25, wherein the one or more processors are configured to execute the machine-readable instructions to:

repeat the determining of the carbon dioxide concentration and the determining of the cardiac output for a plurality of times during a session; and determine a trend in the cardiac output for the session.

Example 46. The system of example 25, wherein the one or more processors are configured to execute the machine-readable instructions to:

determine a background carbon dioxide level for a location of the respiratory treatment apparatus, wherein the determining of the cardiac output of the user is based, at least in part, on the background carbon dioxide level for the location.

Example 47. The system of example 46, wherein the one or more processors are configured to execute the machine-readable instructions to:

determine a worsening in the cardiac output based on the trend; and determine a need for intervention based on the worsening in the cardiac output.

Example 48. The method of example 25, wherein the one or more processors are configured to execute the machine-readable instructions to determine the carbon dioxide concentration within the conduit based on analyzing standing waves and harmonics with the conduit.

5.10 GLOSSARY

For the purposes of the present technology disclosure, in certain forms of the present technology, one or more of the following definitions may apply. In other forms of the present technology, alternative definitions may apply.

5.10.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the respiratory therapy system or patient, and (ii) immediately surrounding the respiratory therapy system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

Leak: The word leak will be taken to be an unintended flow of air. In one example, leak may occur as the result of an incomplete seal between a mask and a patient's face. In another example leak to ambient may occur in a swivel elbow.

Patient: A person, whether or not they are suffering from a respiratory condition.

Pressure: Force per unit area. Pressure may be expressed in a range of units, including $cmH_2O$, $g\text{-}f/cm^2$ and hectopascal. 1 $cmH_2O$ is equal to 1 $g\text{-}f/cm^2$ and is approximately 0.98 hectopascal. In this specification, unless otherwise stated, pressure is given in units of $cmH_2O$.

Respiratory Pressure Therapy (RPT): The application of a supply of air to an entrance to the airways at a treatment pressure that is typically positive with respect to atmosphere.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

5.10.2 Patient Interface

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.11 OTHER REMARKS

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

The term "about" is used herein to refer to quantities that vary by as much as 30%, preferably by as much as 20%, and more preferably by as much as 10% to a reference quantity. The use of the word 'about' to qualify a number is merely an express indication that the number is not to be construed as a precise value.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior technology. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Thus, throughout this specification, unless the context requires otherwise, the words "comprise", "comprises" and "comprising" will be understood to imply the inclusion of a stated step or element or group of steps or elements but not the exclusion of any other step or element or group of steps or elements. Any one of the terms: "including" or "which includes" or "that includes" as used herein is also an open term that also means including at least the elements/features that follow the term, but not excluding others. Thus, "including" is synonymous with and means "comprising".

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a processor readable medium or computer readable storage medium (or multiple such storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs or processor control instructions that, when executed on one or more computers or other processors, perform methods that implement the various embodiments of the technology discussed above. The computer readable medium or media can be transportable, such that the program or programs stored thereon can be loaded onto one or more different computers or other processors to implement various aspects of the present technology as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present technology need not reside on a single computer or processor, but may be distributed in a modular fashion amongst a number of different computers or processors to implement various aspects of the present technology. For example, some versions of the present technology may include a server with access to any of the computer readable or processor-readable mediums as described herein. The server may be configured to receive requests for downloading the processor-control instructions or processor-executable instructions of the medium to an electronic device, such as a smart mobile phone or smart speaker, over a network such as a communications network, an internet or the Internet. Thus, the electronic device may also include such a medium to execute the instructions of the medium. Similarly, the present technology may be implemented as a method of a server having access to any of the mediums described herein. The method(s) may include receiving, at the server, a request for downloading the processor-executable instructions of the medium to an electronic device over the network; and transmitting the instructions of the medium to the electronic device in response to the request. Optionally, the server may have access to the medium to execute the instructions of the medium.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Although the technology herein has been described with reference to particular examples, it is to be understood that these examples are merely illustrative of the principles and applications of the technology. For example, although the acoustic generator(s) and acoustic monitoring techniques are described herein in particular examples concerning the use, and component(s) of, RPT device(s), it will be understood that such acoustic generator(s) and acoustic monitoring techniques may be similarly implemented with the component(s) of any respiratory therapy (RT) device such as a high flow therapy (HFT) device that provides a controlled flow of air at therapeutic flow levels through a patient interface. Thus, the HFT device is similar to a pressure-controlled RPT device but configured with a controller adapted for flow control. In such examples, the acoustic generator(s) may be configured for measuring a gas characteristic associated with the high flow therapy generated by the HFT device and may be integrated to sample the gas flow of a patient circuit, a conduit coupler thereof, and/or a patient interface of the HFT device. Thus, the HFT device may optionally include an acoustic receiver, as well as the processing techniques for acoustic analysis as described herein, for receiving the acoustic/sound signal generated by the acoustic generator implemented HFT device.

In some instances herein, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| 5.12 REFERENCE SIGNS LIST | |
|---|---|
| patient | 1000 |
| conduit | 1010 |
| system component | 1020 |
| RPT device/humidifier | 1040 |
| microphone | 1050 |
| horn | 1060 |
| bed partner | 1100 |
| step | 1110 |
| step | 1120 |
| step | 1130 |
| step | 1140 |
| step | 1150 |
| step | 1160 |
| trace | 1200 |
| peak | 1210 |
| trace | 1250 |
| peak | 1260 |
| portion | 1310 |
| portion | 1320 |
| acoustic signature | 1350 |
| system | 1400 |
| conduit | 1410 |
| acoustic analysis apparatus | 1415 |
| mask | 1420 |
| connection | 1425 |
| connection | 1435 |
| RPT device/humidifier | 1440 |
| first microphone | 1450 |
| second microphone | 1460 |
| process | 1500 |
| step | 1510 |
| step | 1520 |
| step | 1530 |
| acoustic analysis apparatus | 1600 |
| processor(s) | 1602 |
| memory | 1604 |
| display | 1606 |
| control interface | 1608 |
| data interface | 1610 |
| patient interface | 3000 |
| seal - forming structure | 3100 |
| plenum chamber | 3200 |
| structure | 3300 |
| vent | 3400 |
| connection port | 3600 |
| forehead support | 3700 |
| RPT device | 4000 |
| external housing | 4010 |
| upper portion | 4012 |
| portion | 4014 |
| panel | 4015 |
| chassis | 4016 |
| handle | 4018 |
| pneumatic block | 4020 |
| inlet air filter | 4112 |
| inlet muffler | 4122 |
| outlet muffler | 4124 |
| pressure generator | 4140 |
| blower | 4142 |
| air circuit | 4170 |
| electrical components | 4200 |
| PCBA | 4202 |
| electrical power supply | 4210 |
| input devices | 4220 |
| central controller | 4230 |
| therapy device controller | 4240 |
| protection circuits | 4250 |
| memory | 4260 |
| pressure sensor microphone | 4270 |
| data communication interface | 4280 |
| remote external communication network | 4282 |
| local external communication network | 4284 |
| remote external device | 4286 |
| local external device | 4288 |
| output device | 4290 |
| algorithms | 4300 |
| humidifier | 5000 |
| humidifier inlet | 5002 |
| humidifier outlet | 5004 |
| humidifier base | 5006 |
| water reservoir | 5110 |
| conductive portion | 5120 |
| humidifier reservoir dock | 5130 |
| locking lever | 5135 |
| water level indicator | 5150 |
| humidifier transducer | 5210 |
| air pressure sensor | 5212 |
| air flow rate transducer | 5214 |
| temperature sensor | 5216 |
| humidity sensor | 5218 |
| heating element | 5240 |
| controller | 5250 |
| system | 7000 |
| conduit | 7010 |
| mask | 7020 |
| connection | 7025 |
| system | 7030 |
| RPT device/humidifier | 7040 |
| microphone | 7050 |
| input signal component | 8010 |
| reflection component | 8020 |
| method | 11000 |

5.13 CITED REFERENCES

[1] *Partial $CO_2$ rebreathing Fick technique for noninvasive measurement of cardiac output*. Bailey, P. L.; Haryadi, D. G.; Orr, J. A.; Westenskow, D. R. Anesthesia & Analgesia, April 1998, Vol. 86 Issue 4S, page 53 ff.

The invention claimed is:

1. A method of one or more processors for generating a patient and/or system status indication with a respiratory therapy system configured to deliver respiratory therapy to a patient, the respiratory therapy system comprising a flow generator configured to generate a supply of pressurized air along an air circuit to a patient interface, the method comprising:

processing a sound signal representing a sound in the air circuit from a microphone to obtain cepstrum data;

generating a time series of delay estimates based on acoustic signatures of the cepstrum data, wherein each of the acoustic signatures represents a reflection of sound from the patient interface along the air circuit;

analysing variation of the time series of delay estimates; and generating one or more output indicators based on the variation, the one or more output indicators concerning patient and/or system status.

2. The method of claim 1 wherein generating the time series comprises:

separating an acoustic signature from a cepstrum of the cepstrum data;

estimating a delay of the acoustic signature for the time series of delay estimates; and repeating the separating, and estimating.

3. The method of claim 1, wherein the analysing comprises filtering the time series of delay estimates to allow passing of frequencies within a breathing rate frequency band.

4. The method of claim 1, wherein the analysing further comprises converting the time series of delay estimates to indications of concentration of carbon dioxide in the air circuit.

5. The method of claim 1, wherein the one or more output indicators comprises an indication of end-tidal carbon dioxide concentration ($EtCO_2$) of the patient.

6. The method of claim 5, further comprising adjusting a parameter of the respiratory therapy system based on the indication of $EtCO_2$.

7. The method of claim 1, wherein the one or more output indicators comprises an estimate of cardiac output of the patient.

8. The method of claim 7, further comprising applying a modified Fick technique function and measuring change in an indication of $EtCO_2$ generated with the time series of delay estimates to generate the estimate of the cardiac output.

9. The method of claim 7, further comprising repeating the analysing to generate a plurality of estimates of the patient's cardiac output.

10. The method of claim 9, further comprising determining a trend in the plurality of estimates of the patient's cardiac output.

11. The method of claim 10, further comprising taking action based on the determined trend in the plurality of estimates.

12. The method of claim 11, wherein the taking action comprises generating an output communication and/or an output on a display.

13. The method of claim 4, wherein the analysing further comprises:

- determining one or more environmental parameters of the respiratory therapy system; and
- correcting for the one or more environmental parameters during the determining of the carbon dioxide concentration.

14. The method of claim 13, wherein the one or more environmental parameters comprise air temperature, ambient pressure, ambient carbon dioxide concentration, background noise, or a combination thereof.

15. The method of claim 14, wherein the background noise is generated by a sound sensor that is different from a sound sensor that generated the sound signal.

16. The method of claim 1, wherein the analysing comprises removing breathing-rate-frequency-band variations from the time series of delay estimates to obtain a time series of non-respiratory-related delay estimates.

17. The method of claim 16 wherein the one or more output indicators comprises an indication of replacement condition of a component of the air circuit and/or the patient interface.

18. The method of claim 16, wherein the analysing further comprises mapping the time series of non-respiratory-related delay estimates to a time series of values of length of the air circuit.

19. The method of claim 18, wherein the analysing further comprises determining whether an increase in length of the air circuit over many therapy sessions is greater than a threshold.

20. The method of claim 18, wherein the analysing further comprises determining a variability of length of the air circuit over a session of respiratory therapy.

21. The method of claim 1, wherein the processing comprises removing background noise from the environment of the respiratory therapy system from the sound signal.

22. The method of claim 1, wherein the one or more output indicators further comprises:

(a) a control signal for controlling an adjustment of a therapy output of a therapy device; and/or (b) an output communication or an output of a display.

23. A device for generating a patient and/or a system status indication with a respiratory therapy system configured to deliver respiratory therapy to a patient, the respiratory therapy system comprising a flow generator configured to generate a supply of pressurized air along an air circuit to a patient interface, the device comprising:

- a sensor configured to generate a sound signal representing a sound in the air circuit; and
- a controller comprising one or more processors and a memory, wherein the one or more processors are configured by program instructions stored in the memory to execute the method of claim 1.

24. The device of claim 23 further comprising a blower, wherein the controller is configured to control operation of the blower.

25. A device for generating a patient and/or system status indication with a respiratory therapy system configured to deliver respiratory therapy to a patient, the respiratory therapy system comprising a flow generator configured to generate a supply of pressurized air along an air circuit to a patient interface, the device comprising:

- a sensor configured to generate a sound signal representing a sound in the air circuit; and
- a controller configured to:
  - process the sound signal representing a sound in the air circuit to obtain cepstrum data;
  - generate a time series of delay estimates based on acoustic signatures in the cepstrum data, wherein each of the acoustic signatures represents a reflection of sound from the patient interface along the air circuit;
  - analyse variation in the time series of delay estimates; and
  - generate one or more output indicators based on the variation, the one or more output indicators concerning patient and/or system status.

26. The device of claim 25, further comprising a second sensor configured to generate a sound signal representing background noise in an environment of the respiratory therapy system.

27. The device of claim 26, wherein the controller is further configured to remove background noise from the environment of the respiratory therapy system from the generated sound signal representing the sound in the air circuit using the generated sound signal representing the background noise in the environment of the respiratory therapy system.

28. The device of claim 25, wherein to generate the time series, the controller is configured to:

- separate an acoustic signature from a cepstrum of the cepstrum data,
- estimate a delay of the acoustic signature for the time series of delay estimates; and
- repeat the separation, and the estimation.

29. The device of claim 25, wherein to analyse variation, the controller is configured to filter the time series of delay estimates to allow passing of frequencies within a breathing rate frequency band.

30. The device of claim 25, wherein to analyse variation, the controller is configured to convert the time series of delay estimates to indications of concentration of carbon dioxide in the air circuit.

31. The device of claim 25, wherein the one or more output indicators comprises an indication of end-tidal carbon dioxide concentration ($EtCO_2$) of the patient.

32. The device of claim 31, wherein the controller is further configured to adjust a parameter of the respiratory therapy system based on the indication of $EtCO_2$.

33. The device of claim 25, wherein the one or more output indicators comprises an estimate of cardiac output of the patient.

34. The device of claim 33, wherein, the controller is configured to apply a modified Fick technique function and measure change in an indication of $EtCO_2$ generated with the time series of delay estimates to generate the estimate of the cardiac output.

35. The device of claim 33, wherein the controller is configured to repeat the analysing to generate a plurality of estimates of the patient's cardiac output.

36. The device of claim 35, wherein the controller is further configured to determine a trend in the plurality of estimates of the patient's cardiac output.

37. The device of claim 36, wherein the controller is further configured to take action based on the determined trend in the plurality of estimates.

38. The device of claim 37, wherein the action comprises generating an output communication and/or an output on a display.

39. The device of claim 25, wherein to analyse variation, the controller is configured to remove breathing-rate-frequency-band variations from the time series of delay estimates to obtain a time series of non-respiratory-related delay estimates.

40. The device of claim 39 wherein the one or more output indicators comprises an indication of replacement condition of a component of the air circuit and/or the patient interface.

41. The device of claim 39, wherein to analyse variation, the controller is configured to map the time series of non-respiratory-related delay estimates to a time series of values of length of the air circuit.

42. The device of claim 41, wherein to analyse variation, the controller is configured to determine whether an increase in length of the air circuit over many therapy sessions is greater than a threshold.

43. The device of claim 41, wherein to analyse variation, the controller is configured to determine a variability of length of the air circuit over a session of respiratory therapy.

44. The device of any one of claim 25, wherein the one or more output indicators further comprises:

(a) a control signal for controlling an adjustment of a therapy output of a therapy device; and/or (b) an output communication or an output of a display.

45. Apparatus comprising:

means for generating a sound signal representing a sound in an air circuit of a respiratory therapy system, the respiratory therapy system comprising a flow generator configured to generate a supply of pressurized air from an outlet along the air circuit to a patient interface;

means for processing the sound signal representing a sound in the air circuit, to obtain cepstrum data;

means for generating a time series of delay estimates based on acoustic signatures in the cepstrum data, wherein each of the acoustic signatures represents a reflection of sound from the patient interface along the air circuit;

means for analysing variation of the time series of delay estimates; and means for generating one or more output indicators based on the variation, the one or more output indicators concerning patient and/or system status.

46. A method of one or more processors for generating a status indication about a patient interface associated with a respiratory therapy system configured to deliver respiratory therapy to a patient, the respiratory therapy system comprising a flow generator configured to generate a supply of pressurized air along an air circuit to the patient interface, the method comprising:

processing a sound signal representing a sound in the air circuit, to obtain cepstrum data;

separating an acoustic signature from the cepstrum data, the acoustic signature representing a reflection of sound from the patient interface along the air circuit;

estimating an internal delay of the acoustic signature, wherein the internal delay is a delay between two portions of the acoustic signature representing reflections from respective components of the patient interface separated by a mask tube;

repeating the processing, separating, and estimating to generate a time series of estimates of the internal delay;

analysing the time series of internal delay estimates; and generating one or more output indicators based on the analysing, the one or more output indicators concerning patient interface status.

47. The method of claim 46, wherein the analysing comprises filtering the time series of internal delay estimates to allow passing of frequencies within a breathing rate frequency band.

48. The method of claim 47, wherein the analysing further comprises analysing the filtered time series of internal delay estimates to generate an indication of concentration of carbon dioxide in the mask tube.

49. The method of claim 46, wherein the analysing comprises removing breathing-rate-frequency-band variations from the time series of internal delay estimates to obtain a time series of non-respiratory-related internal delay estimates.

50. The method of claim 49, wherein the analysing further comprises mapping the time series of non-respiratory-related internal delay estimates to a time series of values of length of the mask tube.

51. The method of claim 50, wherein the analysing further comprises determining whether an increase in the length of the mask tube over many therapy sessions is greater than a threshold.

52. The method of claim 50, wherein the analysing further comprises determining a variability of the length of the mask tube over a session of respiratory therapy.

53. A device for generating a status indication about a patient interface associated with a respiratory therapy system configured to deliver respiratory therapy to a patient, the respiratory therapy system comprising a flow generator configured to generate a supply of pressurized air along an air circuit to the patient interface, the device comprising:

a sensor configured to generate a sound signal representing a sound in the air circuit; and a controller comprising one or more processors and a memory, wherein the one or more processors are configured by program instructions stored in the memory to execute the method of claim 46.

54. A device for generating a status indication about a patient interface for a respiratory therapy system configured to deliver respiratory therapy to a patient, the respiratory therapy system comprising a flow generator configured to generate a supply of pressurized air along an air circuit to the patient interface, the device comprising:

a sensor configured to generate a sound signal representing a sound in the air circuit; and a controller configured to:

process the sound signal representing a sound in the air circuit, to obtain cepstrum data;

separate an acoustic signature from the cepstrum data, the acoustic signature representing a reflection of sound from the patient interface along the air circuit;

estimate an internal delay of the acoustic signature, wherein the internal delay is a delay between two portions of the acoustic signature, each portion representing a reflection from a corresponding component of the patient interface separated by a mask tube;

repeat the processing, separating, and estimating to generate a time series of estimates of the internal delay;

analyse the time series of internal delay estimates; and generate one or more output indicators based on the analysing, the one or more output indicators concerning patient interface status.

55. The device of claim 54, wherein to analyse the time series, the controller is configured to filter the time series of internal delay estimates to allow passing of frequencies within a breathing rate frequency band.

56. The device of claim 55, wherein to analyse the time series, the controller is further configured to analyse the filtered time series of internal delay estimates to generate an indication of concentration of carbon dioxide in the mask tube.

57. The device of claim 54, wherein to analyse the time series, the controller is configured to remove breathing-rate-frequency-band variations from the time series of internal delay estimates to obtain a time series of non-respiratory-related internal delay estimates.

58. The device of claim 57, wherein to analyse the time series, the controller is further configured to map the time series of non-respiratory-related internal delay estimates to a time series of values of length of the mask tube.

59. The device of claim 58, wherein to analyse the time series, the controller is further configured to determine whether an increase in the length of the mask tube over many therapy sessions is greater than a threshold.

60. The device of claim 59, wherein to analyse the time series, the controller is further configured to determine a variability of the length of the mask tube over a session of respiratory therapy.

61. Apparatus comprising:

means for generating a sound signal representing a sound in an air circuit of a respiratory therapy system, the respiratory therapy system comprising a flow generator configured to generate a supply of pressurized air from an outlet along the air circuit to a patient interface;

means for processing the sound signal representing a sound in the air circuit, to obtain cepstrum data;

means for separating an acoustic signature from the cepstrum, the acoustic signature representing a reflection of sound from the patient interface along the air circuit;

means for estimating an internal delay of the acoustic signature, wherein the internal delay is a delay between two portions of the acoustic signature, each portion representing a reflection from a corresponding component of the patient interface separated by a mask tube;

means for repeating the processing, separating, and estimating to generate a time series of estimates of the internal delay;

means for analysing the time series of internal delay estimates; and means for generating one or more output indicators based on the analysing, the one or more output indicators concerning patient interface status.

62. A respiratory therapy system for delivering respiratory therapy to a patient, the system comprising:

a flow generator configured to generate a supply of pressurized air;

an air circuit connected to the flow generator so as to convey the supply of pressurised air to a patient interface; and a device for generating a patient and/or system status indication with the respiratory therapy system, the device according to claim 25.

63. A respiratory therapy system for delivering respiratory therapy to a patient, the system comprising:

a flow generator configured to generate a supply of pressurized air;

an air circuit connected to the flow generator so as to convey the supply of pressurised air to a patient interface; and a device for generating a status indication about the patient interface, the device according to claim 54.

* * * * *